(12) United States Patent
Onishi

(10) Patent No.: US 12,156,729 B2
(45) Date of Patent: Dec. 3, 2024

(54) HUMAN BODY DETECTION DEVICE, BED DEVICE, AND HUMAN BODY DETECTION SYSTEM

(71) Applicant: MITSUI CHEMICALS, INC., Tokyo (JP)

(72) Inventor: Katsuki Onishi, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 843 days.

(21) Appl. No.: 17/271,649

(22) PCT Filed: Sep. 10, 2019

(86) PCT No.: PCT/JP2019/035534
§ 371 (c)(1),
(2) Date: Feb. 26, 2021

(87) PCT Pub. No.: WO2020/059573
PCT Pub. Date: Mar. 26, 2020

(65) Prior Publication Data
US 2021/0338111 A1    Nov. 4, 2021

(30) Foreign Application Priority Data

Sep. 19, 2018    (JP) .................................. 2018-175421

(51) Int. Cl.
*A61B 5/11*    (2006.01)
*A61B 5/00*    (2006.01)
(Continued)

(52) U.S. Cl.
CPC .......... *A61B 5/1115* (2013.01); *A61B 5/6892* (2013.01); *G08B 21/0461* (2013.01); *H10N 30/30* (2023.02); *H10N 30/60* (2023.02)

(58) Field of Classification Search
CPC .... H10N 30/857; H10N 30/302; H10N 30/60; H10N 30/30; A61B 5/6892; A61B 5/1115
See application file for complete search history.

(56) References Cited

U.S. PATENT DOCUMENTS

| | | |
|---|---|---|
| 4,984,222 A | 1/1991 | Beauducel et al. |
| 5,571,961 A | 11/1996 | Gassner et al. |
| (Continued) | | |

FOREIGN PATENT DOCUMENTS

| | | |
|---|---|---|
| JP | H0277676 A | 3/1990 |
| JP | H06269427 A | 9/1994 |
| (Continued) | | |

OTHER PUBLICATIONS

International Search Report (PCT/ISA/210) issued on Nov. 19, 2019, by the Japanese Patent Office as the International Searching Authority for International Application No. PCT/JP2019/035534 and an English translation of the Report. (4 pages).

(Continued)

*Primary Examiner* — J. San Martin
(74) *Attorney, Agent, or Firm* — BUCHANAN, INGERSOLL & ROONEY PC

(57) ABSTRACT

A human body detection device including line-shaped piezoelectric substrates respectively provided in each of a plurality of regions in a plate material intersecting a direction of pressure received from a human body, and provided such that an axial direction of each of the piezoelectric substrates runs along the plate material so as to detect pressure applied in a radial direction of the piezoelectric substrate, memory, and a processor coupled to the memory. The processor is configured to be capable of detecting an output signal from each of the piezoelectric substrates.

15 Claims, 18 Drawing Sheets

(51) Int. Cl.
*G08B 21/04* (2006.01)
*H10N 30/30* (2023.01)
*H10N 30/60* (2023.01)

(56) References Cited

U.S. PATENT DOCUMENTS

| | | | |
|---|---|---|---|
| 8,648,151 | B2 | 2/2014 | Yoshida et al. |
| 2004/0111045 | A1 | 6/2004 | Sullivan et al. |
| 2007/0008156 | A1 | 1/2007 | Ueda et al. |
| 2008/0169931 | A1* | 7/2008 | Gentry ............... A61B 5/1117 600/300 |
| 2011/0068928 | A1 | 3/2011 | Riley et al. |
| 2017/0245799 | A1* | 8/2017 | Fleischer ............ A61B 5/447 |
| 2017/0333274 | A1* | 11/2017 | Riley ............... A61B 5/02055 |
| 2018/0108826 | A1 | 4/2018 | Tajitsu et al. |
| 2019/0003905 | A1 | 1/2019 | Yoshida et al. |
| 2019/0214542 | A1* | 7/2019 | Yoshida ............ H10N 30/302 |
| 2020/0058844 | A1* | 2/2020 | Tanimoto ........... H10N 30/20 |

FOREIGN PATENT DOCUMENTS

| | | | |
|---|---|---|---|
| JP | H07174648 | A | 7/1995 |
| JP | H10229973 | A | 9/1998 |
| JP | 2003230605 | A | 8/2003 |
| JP | 2004154242 | A * | 6/2004 |
| JP | 2005007067 | A | 1/2005 |
| JP | 2005351781 | A | 12/2005 |
| JP | 2006512112 | A | 4/2006 |
| JP | 2006284263 | A | 10/2006 |
| JP | 2011136145 | A | 7/2011 |
| JP | 2016123615 | A | 7/2016 |
| WO | 2017111108 | A1 | 6/2017 |

OTHER PUBLICATIONS

Written Opinion (PCT/ISA/237) issued on Nov. 19, 2019, by the Japanese Patent Office as the International Searching Authority for International Application No. PCT/JP2019/035534. (8 pages).

* cited by examiner

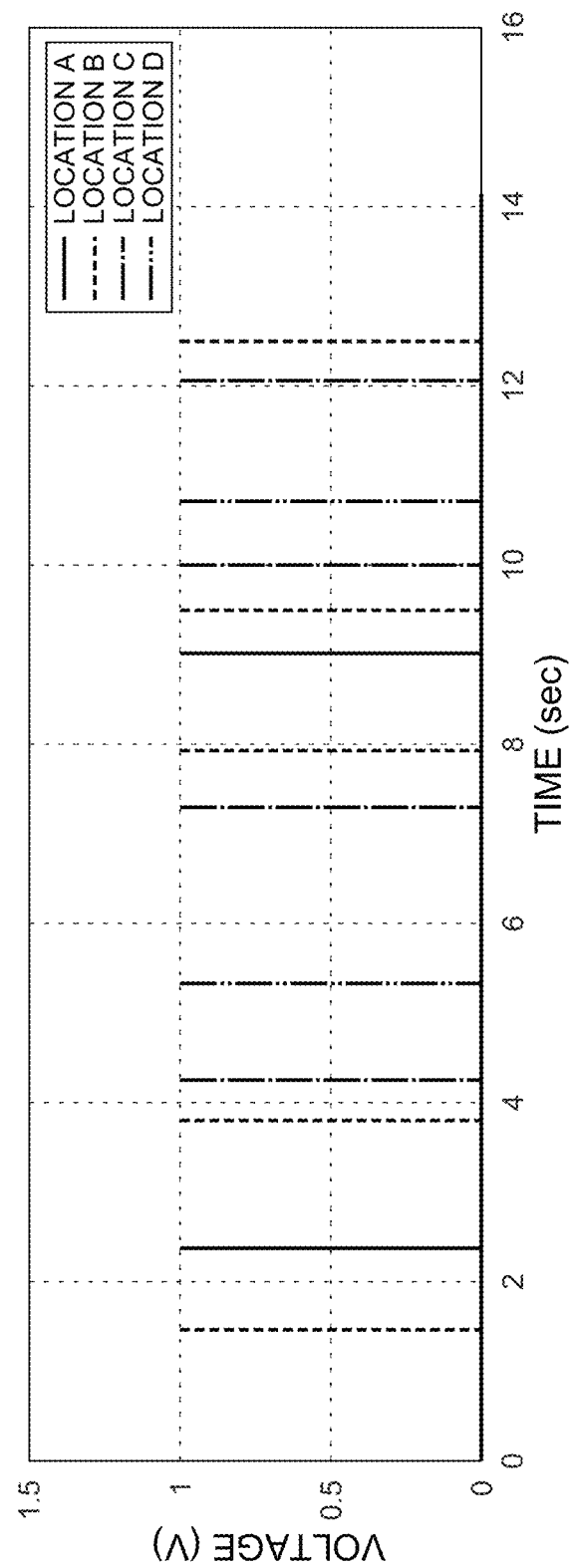

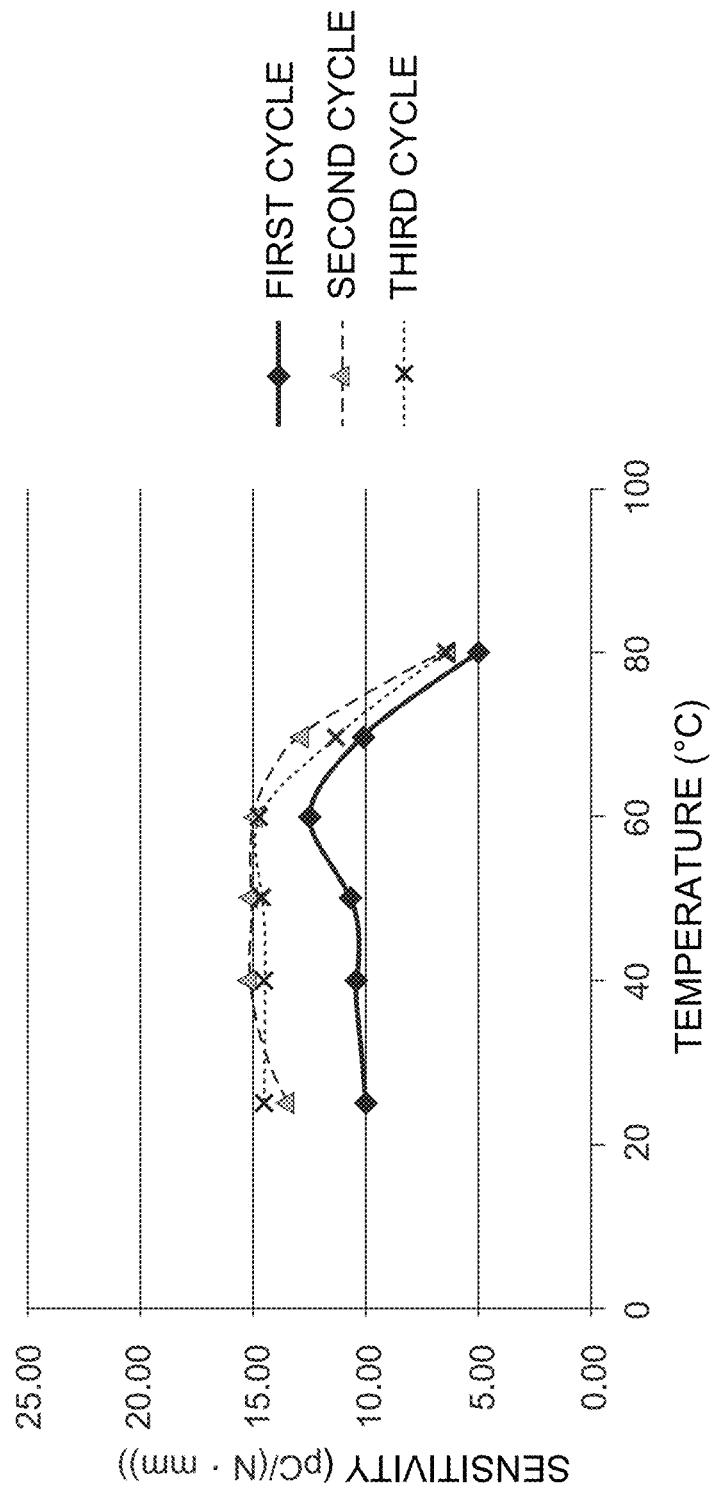

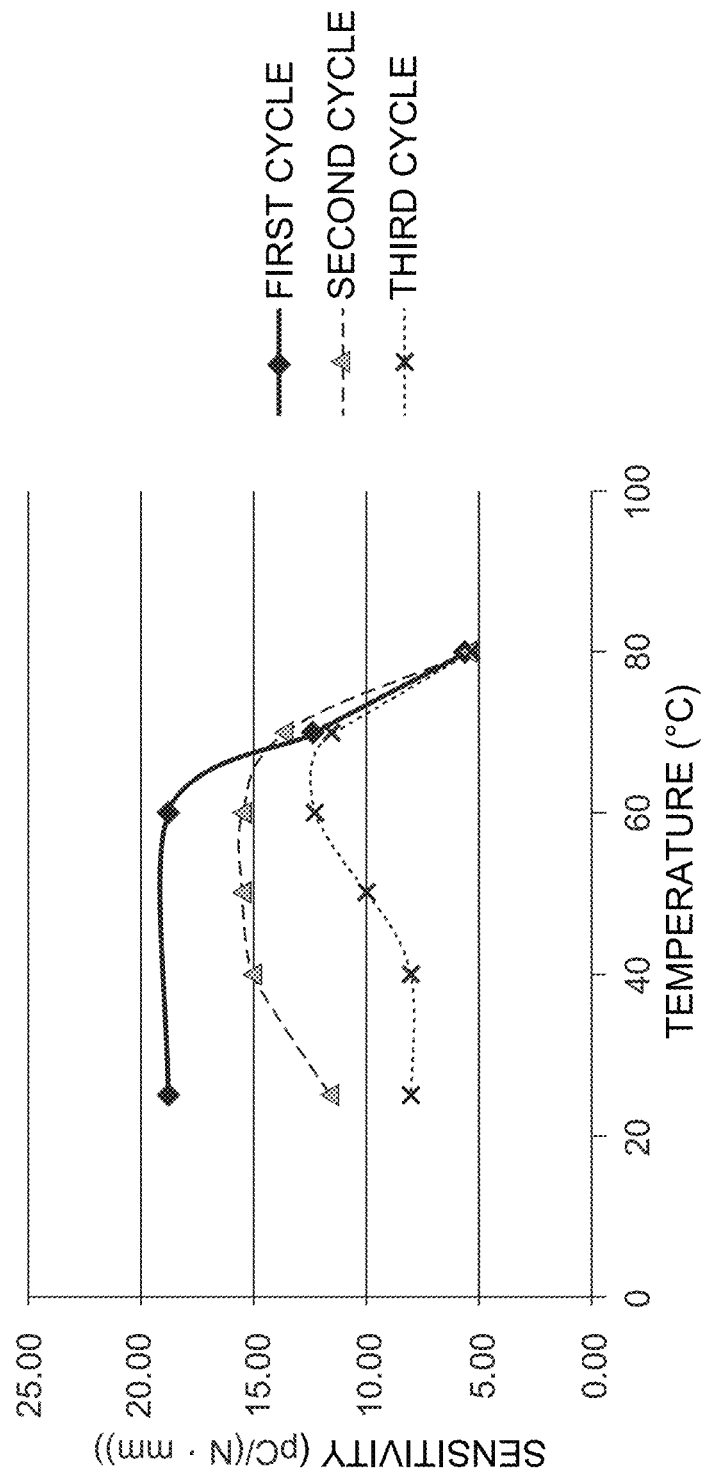

HUMAN BODY DETECTION DEVICE, BED DEVICE, AND HUMAN BODY DETECTION SYSTEM

FIELD

The present disclosure relates to a human body detection device, a bed device, and a human body detection system.

BACKGROUND ART

Recently, consideration is being given to providing beds installed in hospitals or various care facilities etc. with pressure sensors to detect the presence or absence of a care subject who is a person in bed and to detect changes in the physical condition thereof. For example, Patent Document 1 discloses a bed device in which a piezoelectric cable arranged in a wavy pattern is incorporated in a mattress to enable the body of the person in bed to be detected by piezoelectric cable. In another example, Patent Document 2 discloses a biometric monitoring device in which an elongate tape shaped piezoelectric sensor is installed across the width direction on an upper face of a bed. The body of a person in bed is detected by this piezoelectric sensor, and the blood pressure and severity of arteriosclerosis of the person in bed is determined.

Patent Document 1: Japanese Patent Application Laid-Open (JP-A) No. 2005-351781
Patent Document 2: JP-A No. H10-229973

SUMMARY OF INVENTION

Technical Problem

In the device of Patent Document 1, however, since the piezoelectric cable arranged in a wavy pattern is incorporated into the mattress, although the presence or absence of the person in bed can be detected, it is not possible to detect lopsided positioning on the bed of the person in bed. Moreover, in the device of Patent Document 2, the elongate tape shaped piezoelectric sensor is installed across the bed in the width direction, and although the presence or absence of the person in bed can be detected, it is not possible to detect lopsided positioning on the bed of the person in bed.

In consideration of the above circumstances, an object of the present disclosure is to provide a human body detection device, a bed device, and a human body detection system capable of detecting the position on a bed surface of a person in bed using a material with piezoelectric properties.

Solution to Problem

Specific ways to address the above problem are as follows.
<1> A human body detection device including line-shaped piezoelectric substrates respectively provided in each of plural regions in a plate material intersecting a direction of pressure received from a human body, and provided such that an axial direction of each of the piezoelectric substrates runs along the plate material so as to detect pressure applied in a radial direction of the piezoelectric substrate, memory, and a processor coupled to the memory. The processor is configured to be capable of detecting an output signal from each of the piezoelectric substrates.
<2> The human body detection device of <1>, wherein each of the piezoelectric substrates includes an elongate conductor, and an elongate piezoelectric material helically wound in one direction around the conductor, and pressure input to the piezoelectric material is detected from a difference in potential between the conductor and the piezoelectric material.
<3> The human body detection device of <2>, wherein an organic piezoelectric material is employed as the piezoelectric material.
<4> The human body detection device of <3>, wherein the piezoelectric material is an optically active helical chiral polymer (A).
<5> The human body detection device of <4>, wherein the helical chiral polymer (A) is polylactic acid.
<6> The human body detection device of any one of <2> to <5>, wherein each of the piezoelectric substrates includes a covering member at a periphery of the piezoelectric material.
<7> The human body detection device of any one of <1> to <6>, further including a pressing section running along the plate material so as to contact the piezoelectric substrates and be pressed by contact with the human body, and a base portion adjacent to the piezoelectric substrates and on a side facing toward the pressing section.
<8> The human body detection device of <7>, wherein a thickness of the pressing section is in a range of from 0.005 mm to 200 mm, and a hardness of the pressing section is in a range of from 50 N to 200 N as measured in accordance with Method A defined in JIS K 6400-2.
<9> The human body detection device of <7> or <8>, wherein the pressing section, the piezoelectric substrates, and the base portion are arranged along a direction in which the pressing section is pressed.
<10> The human body detection device of any one of <7> to <9>, wherein a foamed plastic is employed as the base portion.
<11> The human body detection device of any one of <1> to <10>, wherein each of the piezoelectric substrates is a biometric information acquisition device.
<12> The human body detection device of any one of <1> to <11>, wherein each of the piezoelectric substrates has a non-circular cross-section profile in a cross-section taken perpendicular to the axial direction of the piezoelectric substrate.
<13> The human body detection device of <12>, wherein, in a cross-section taken perpendicular to the axial direction of the piezoelectric substrate, each piezoelectric substrate has a dimensional ratio of a major axis with respect to a minor axis of from 1.05 to 10.00.
<14> A bed device including the human body detection device of any one of <1> to <13>.
<15> A human body detection system including the human body detection device of any one of <1> to <13>, the regions provided along a predetermined direction in the plate material, and the piezoelectric substrates arranged in each of the regions. The processor is configured to determine movement of the human body above the plate material by comparing output signals from piezoelectric substrates that are adjacent to each other in the predetermined direction.

Advantageous Effects

The present disclosure enables detection of the position of a person in bed.

BRIEF DESCRIPTION OF DRAWINGS

FIG. 14 is a graph illustrating output when the voltages output exceed a threshold value in the measurement results of FIG. 13.

FIG. 16A is a graph illustrating results of temperature characteristic evaluation for a piezoelectric substrate of Example 2.

FIG. 16B is a graph illustrating results of temperature characteristic evaluation for a piezoelectric substrate of Example 3.

DESCRIPTION OF EMBODIMENTS

Explanation follows regarding embodiments of the present disclosure. Note that the present disclosure is not limited to the following embodiments.

Herein, a numerical range represented by "from A to B" means a range including numerical values A and B as a lower limit value and an upper limit value, respectively.

Herein, "principal faces" of each of the elongate-flat-plate-shaped piezoelectric materials (a first piezoelectric material and a second piezoelectric material) means faces perpendicular to the thickness direction of the elongate-flat-plate-shaped piezoelectric material (i.e., faces including a lengthwise direction and a width direction thereof).

Herein, a "face" of a member means a "principal face" of the member unless otherwise specified.

Herein, a thickness, a width, and a length satisfy a relationship of thickness<width<length, as in the usual definitions thereof.

Herein, an angle formed between two line segments is expressed in a range of from 0° to 90°.

Herein, "film" is a concept including so-called "sheets" as well as so-called "films".

First Embodiment

As a first embodiment, explanation follows regarding a bed device 10 configuring a human body detection system, and a human body detection device 30 provided to the bed device 10, with reference to FIG. 1 to FIG. 8.

Configuration of Bed Device

Figure 1:
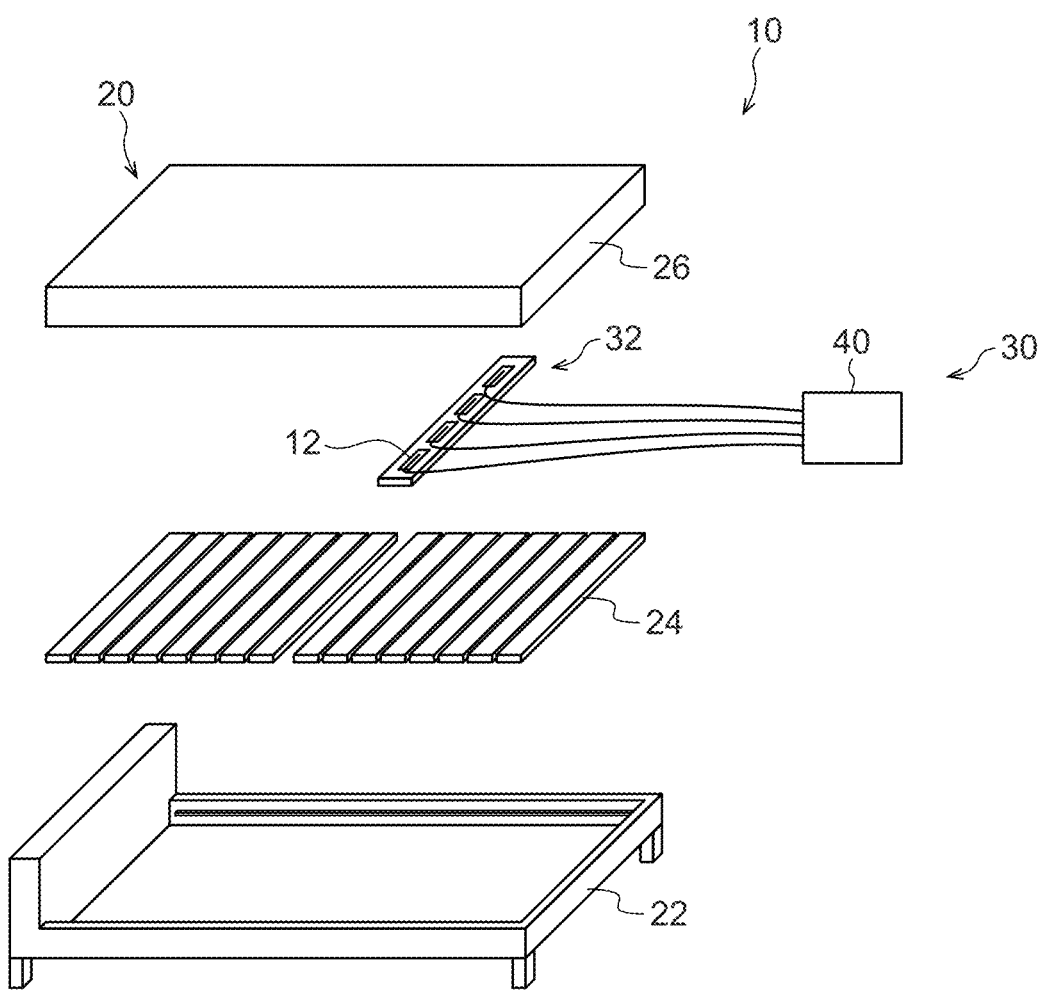
FIG. 1 is an exploded perspective view of a bed device according to a first embodiment.

As illustrated in FIG. 1, the bed device 10 of the present embodiment includes a bed 20 provided with legs, and the human body detection device 30. The bed 20 includes a frame-shaped frame 22 installed on the floor, a pair of bed boards 24, serving as a plate material that cover a central portion of the frame 22, and a mattress 26 placed on an upper face of the bed boards 24.

The bed boards 24 are duck boards formed by laying rectangular slats next to one another in the bed lengthwise direction of the bed device 10. The bed boards 24 are also arranged next to each other in the bed lengthwise direction.

The mattress 26 is configured by sheet-shaped urethane foam covered with a polyester fabric. The mattress 26 is placed above the bed boards 24 and above a sensor unit 32, described later, and a person in bed lies in a recumbent position on an upper face of the mattress 26. The mattress 26 of the present embodiment contacts a piezoelectric substrate 12 covered with an insulating member 38 that is a covering member, and corresponds to a pressing section that is pressed when contacted by the body of the person in bed.

Although the portion of the mattress 26 pressed in the present embodiment is made from urethane (urethane foam), there is no limitation thereto, and this portion of the mattress 26 may be made of fiber or latex. The pressing section does not necessarily have to be the mattress 26 provided to of the bed 20, and may be configured by a sheet or mat. The thickness of the pressing section is in a range of from 0.005 mm to 200 mm, and the hardness of the pressing section is in a range of from 50 N to 200 N as measured according to Method A as defined in JIS K 6400-2, is preferably in a range of from 100 N to 200 N, and is more preferably in a range of from 110 N to 170 N.

The hardness of the mattress 26 of the present embodiment is determined in the following manner according to Method A as defined in JIS K 6400-2. Namely, the hardness of the mattress 26 is determined by laying the internal foam of the mattress 26 flat, placing a cylindrical pressing board with a 200 mm diameter thereon, and pushing the cylindrical pressing board in to a distance of 75% of the original thickness of the foam. The pressing board is then retracted to the original position and then pushed in to a distance of 40% of the original thickness of the foam, and a load value in Newtons (N) is found after remaining static for 30 seconds.

The bed device 10 of the present embodiment functions as the bed 20 configured by the frame 22, the pair of bed boards 24, and the mattress 26 as described above, however the position of a human body on the bed can moreover be detected by installing the sensor unit 32 between the bed boards 24 and the mattress 26.

Configuration of Human Body Detection Device

Figure 2:
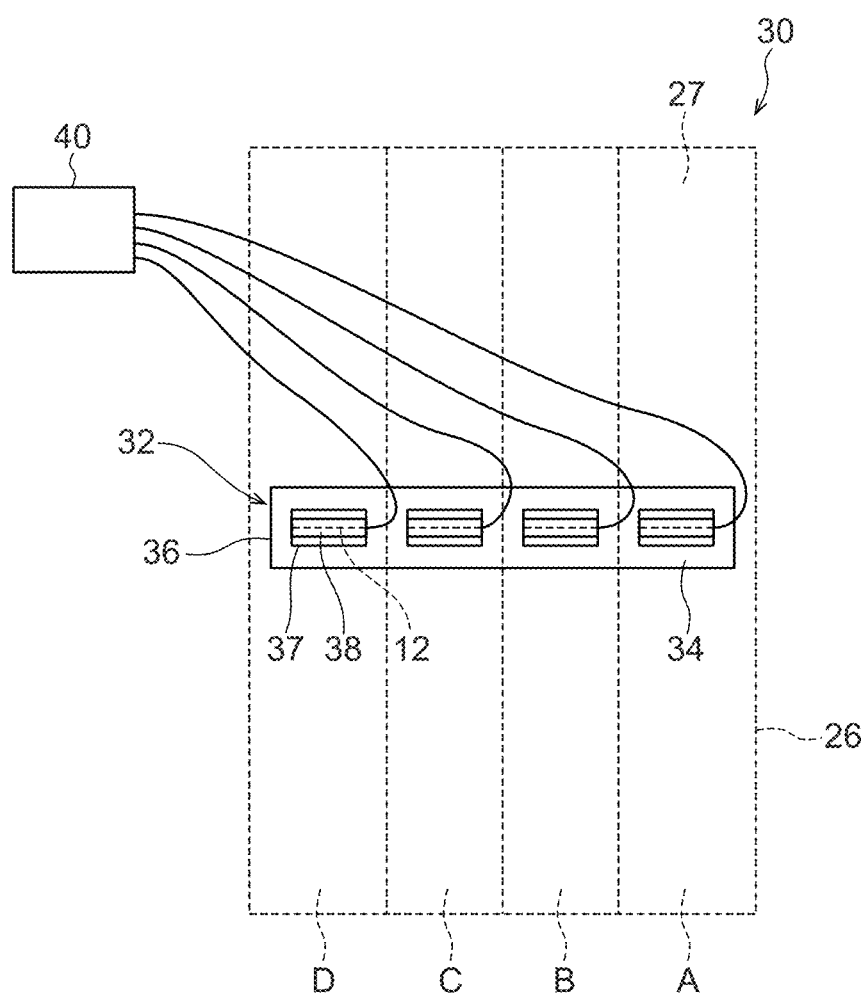
FIG. 2 is a plan view of a human body detection device provided to a bed device according to the first embodiment.
Figure 3:
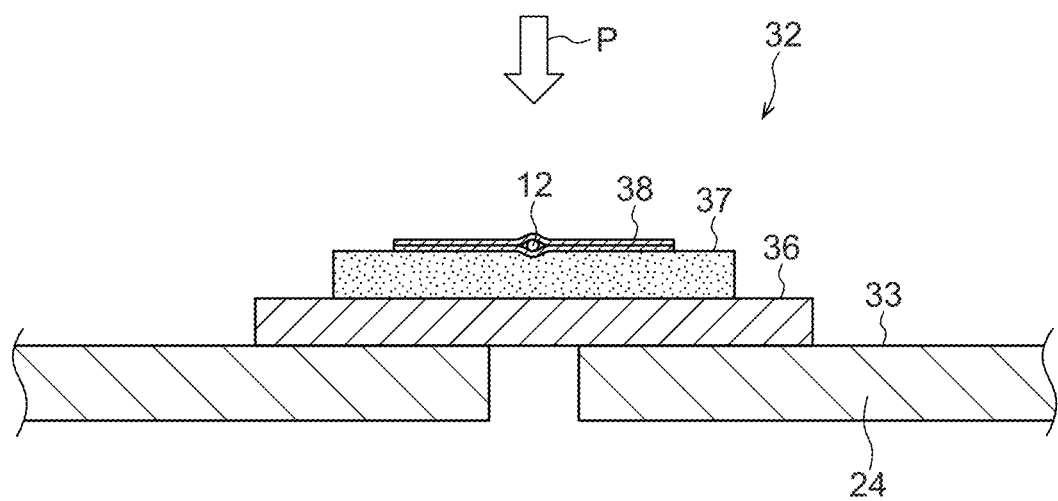
FIG. 3 is a cross-section of a detection section of a human body detection device.

The human body detection device 30 of the present embodiment includes the mattress 26, serving as the pressing section, the sensor unit 32 installed between the bed boards 24 and the mattress 26 so as to be capable of detecting pressure, and an information processing unit 40 including a detection section configured to detect an output signal from the sensor unit 32. As illustrated in FIG. 2 and FIG. 3, the sensor unit 32 is plate shaped and is installed on the bed boards 24 with its lengthwise direction along the bed width direction. Namely, the sensor unit 32 is installed in a direction intersecting the direction of a recumbent human body. The sensor unit 32 is formed so as to be capable of detecting pressure (see arrow P) applied in a direction intersecting a reference plane 33, the reference plane 33 being configured as a plane in which the sensor unit 32 is installed to the bed boards 24 (see FIG. 3). As illustrated in FIG. 2, the sensor unit 32 of the present embodiment is partitioned along its lengthwise direction into four regions 34. A cable shaped piezoelectric substrate 12 to detect pressure is installed in each of the regions 34 along the lengthwise direction of the sensor unit 32 (the bed width direction). A pressure detection range of the mattress 26 is thus divided into four in the bed width direction. The mattress 26 of the present embodiment includes locations A to D serving as detection regions 27 corresponding to each of the regions 34 (or the piezoelectric substrates 12).

The sensor unit 32 includes a support plate 36 (see FIG. 3) placed on the bed boards 24, shock absorbing material 37, serving as a base portion covering an upper face of the support plate 36, and the piezoelectric substrates 12 disposed on an upper face of the shock absorbing material 37 and each having a periphery covered by the corresponding insulating member 38. The support plate 36 is a plate shaped member configured to support the piezoelectric substrates 12 and the shock absorbing materials 37. The length of the support plate 36 in the bed width direction is slightly shorter than the width of the bed boards 24. As illustrated in FIG. 3, the support plate 36 of the present embodiment is installed on the bed boards 24 so as to straddle between the bed boards 24 that have been arranged next to each other in the bed lengthwise direction.

The shock absorbing materials 37 are spongey sheets provided to alleviate tension applied to the piezoelectric substrate 12. The shock absorbing materials 37 are adhered to the support plate 36 in each of the regions 34. The piezoelectric substrates 12 covered by the insulating member 38 make contact with the upper faces of the shock absorbing materials 37. In the sensor unit 32 of the present exemplary embodiment, the mattress 26, the piezoelectric substrates 12, and the shock absorbing materials 37 are arranged in this manner in this sequence along a direction of pressing by the body of the person in bed (namely, the direction of arrow P). The shock absorbing materials 37 are provided on the opposite side of the mattress 26 with the piezoelectric substrates 12 interposed therebetween.

Note that although there is a shock absorbing material 37 provided for each of the regions 34 in the present embodiment, there is no limitation thereto, and a single sheet of the shock absorbing material 37 may be adhered to the support plate 36 so as to straddle all of the regions 34.

Examples of the insulating member 38 include commercial adhesive tapes, flexible insulating films, adhesive films, and the like. The piezoelectric substrate 12 of the present embodiment is covered so as to be sandwiched between a pair of insulating films. Examples of materials that may be employed as the insulating member 38 include base members configured from biaxially oriented nylon films, polyimide films, polyethylene terephthalate films, polyphenylene sulfide films, polysulfone sulfide films, polyester films, polystyrene films, and the like having a Young's modulus of from 2.0 GPa to 10 GPa, and a thickness of from 4 µm to 50 µm, coated with an acrylic- or silicone-based adhesive, with an adhesive strength of from 5.0 N to 30 N.

Figure 4:
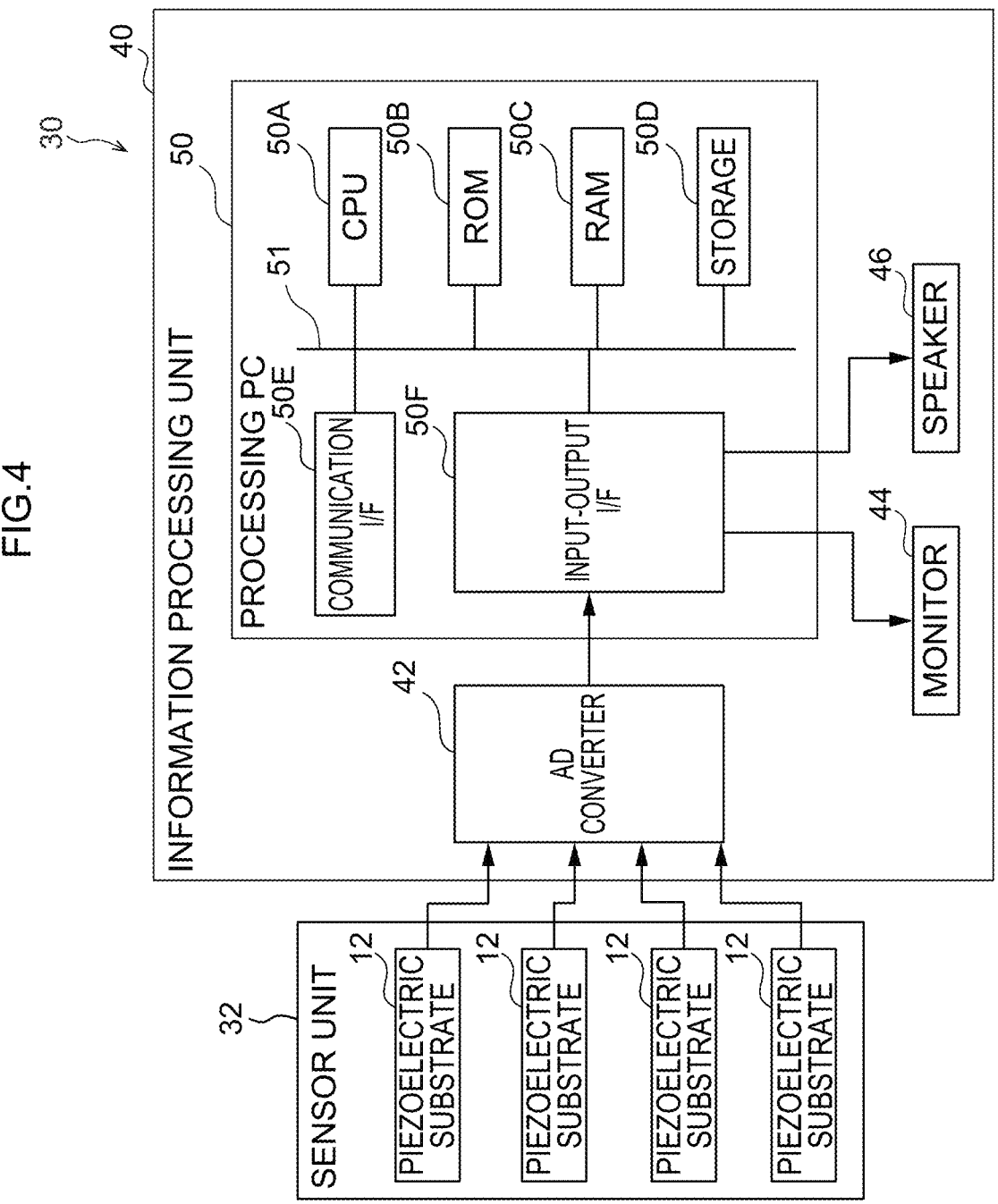
FIG. 4 is a block diagram illustrating a hardware configuration of an information processing unit.

As illustrated in FIG. 4, the information processing unit 40 includes an AD converter 42 configured to convert voltage output of an analog signal output from each of the piezoelectric substrates 12 into a digital signal, and a processing PC 50 configured to detect the digital signal as converted for each of the piezoelectric substrates 12. The AD converter 42 is provided with plural input terminals for inputting the analog signals, and the piezoelectric substrates 12 are electrically connected to the respective input terminals.

The processing PC 50 is configured including a central processing unit (CPU) 50A, read only memory (ROM) 50B, random access memory (RAM) 50C, storage 50D, a communication interface (I/F) 50E, and an input-output I/F 50F. The CPU 50A, the ROM 50B, the RAM 50C, the storage 50D, the communication I/F 50E, and the input-output I/F 50F are connected so as to be capable of communicating with each other through a bus 51.

Note that the CPU 50A corresponds to a processor, and the RAM 50C corresponds to memory.

The CPU 50A is a central processing unit that executes various programs in order to control each section. Namely, the CPU 50A reads a program from the ROM 50B or the storage 50D, and executes the program using the RAM 50C as a workspace. In the present embodiment, an execution program to execute various processing is stored in the storage 50D. The CPU 50A functions as a detection section 55, a determination section 56, and a notification section 57 illustrated in FIG. 5 by executing this execution program.

The ROM 50B is stored with various programs and various data. The RAM 50C serves as a workspace in which programs and data are temporarily stored. The storage 50D serving as a storage section is configured by a hard disk drive (HDD) or a solid state drive (SSD), and is stored with various programs including an operating system and various data.

The communication I/F 50E is an interface used to communicate with a portable terminal such as a smartphone, and employs a protocol such as Ethernet (registered trademark), FDDI, or Wi-Fi (registered trademark).

The input-output I/F 50F is an interface used to communicate with various devices configuring the information processing unit 40. The AD converter 42, a monitor 44, and a speaker 46 are connected to the processing PC 50 of the present embodiment through the input-output I/F 50F.

Figure 5:
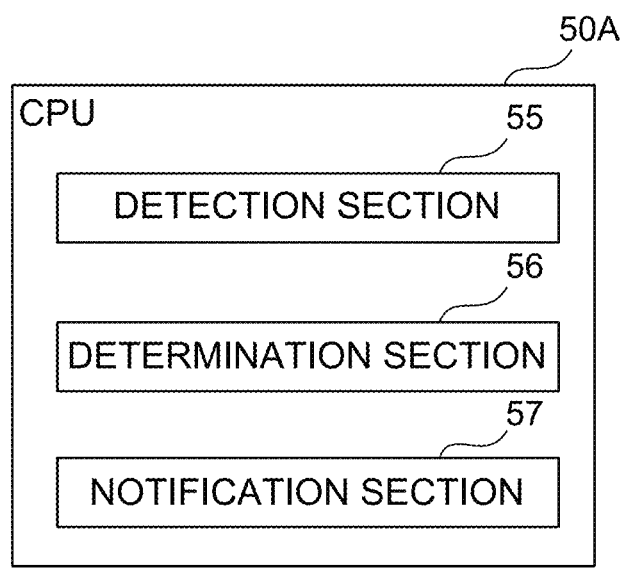
FIG. 5 is a block diagram illustrating an example of functional configuration of a CPU of a processing PC.

FIG. 5 is a block diagram illustrating an example of a functional configuration of the CPU 50A. As illustrated in FIG. 5, the CPU 50A includes the detection section 55, the determination section 56, and the notification section 57. Each part of the functional configuration is implemented by the CPU 50A reading the execution program stored in the storage 50D and executing the execution program.

The detection section 55 has functionality to detect digital signals from each of the piezoelectric substrates 12 as output from the AD converter 42 via the communication I/F 50E. This enables where the body of the person in bed is positioned on the detection region 27 of the bed 20 to be detected. The detection section 55 converts the detected data into numerical values. This enables the amount of pressure applied to each of the detection regions 27 to be ascertained.

The determination section 56 has functionality to compare output signals from adjacent of the piezoelectric substrates 12 so as to dynamically identify the position of the body of the person in bed. For example, in cases in which the voltage output of one of the piezoelectric substrate 12 has decreased while the voltage output of the piezoelectric substrate 12 adjacent thereto has increased, the determination section 56 determines that the person in bed has turned over in bed. In cases in which the voltage output of all of the piezoelectric substrates 12 has decreased, the determination section 56 determines that the person in bed has got up from the bed device 10. Moreover, in cases in which the voltage output of the piezoelectric substrates 12 at the two bed width direction ends is large, the determination section 56 determines that the person in bed is sleeping lopsided.

The notification section 57 has functionality to notify determination results of the determination section 56 relating to turning over in bed, getting up, and lopsided sleeping positions. For example, the notification section 57 may transmit determination results to a mobile telephone of a carer via the communication IN 50E. Alternatively, for example, the notification section 57 may output text information relating to the determination results to the monitor 44 via the communication I/F 50E, or may output audio information relating to the determination results to the speaker 46.

Piezoelectric Substrate

Explanation follows regarding an outline of the piezoelectric substrates employed in pressure detection in the bed device 10 of the present embodiment.

Each of the piezoelectric substrates of the present embodiment includes an elongate conductor, and an elongate first piezoelectric material wound helically in one direction around the conductor.

An organic piezoelectric material may be employed as the first piezoelectric material, with either low-molecular materials or polymer materials being adopted for the organic piezoelectric material. Examples of such organic piezoelectric materials include polyvinylidene fluoride or a polyvinylidene fluoride-based copolymer, polyvinylidene cyanide or a vinylidene cyanid-based copolymer, an odd NYLON such as NYLON 9, NYLON 11, an aromatic NYLON, an alicyclic NYLON, or a helical chiral polymer such as polylactic acid, a polyhydroxycarboxylic acid such as polyhydroxybutyrate, a cellulose-based derivative, polyurea or the like.

From the perspective of good piezoelectric characteristics, workability, and ease of sourcing, the first piezoelectric material is preferably a polymer organic piezoelectric material, and in particular an optically active helical chiral polymer.

The piezoelectric substrate of the present embodiment includes the first piezoelectric material being an optically active helical chiral polymer (A) (also referred to simply as the "helical chiral polymer (A)" hereafter), the lengthwise direction of the first piezoelectric material and the principal orientation direction of the helical chiral polymer (A) included in the first piezoelectric material being substantially parallel to each other, and a degree of orientation F of the first piezoelectric material being in a range from 0.5 up to but not including 1.0, determined from X-ray diffraction measurement by the following Formula (a): Herein, the degree of orientation F=(180°−α)/180° . . . (a)

Wherein α represents a half width of a peak derived from orientation. The unit of α is °.

In the following description of the piezoelectric substrate of the present embodiment, "elongate conductor" may be simply referred to in the description as "conductor", and "elongate first piezoelectric material" may be simply referred to in the description as "first piezoelectric material".

Here, the degree of orientation F of the first piezoelectric material is an index indicating the degree of orientation of the helical chiral polymer (A) included in the first piezoelectric material, such as a degree of orientation in a c-axis measured by a wide-angle X-ray diffractometer (RINT 2550 manufactured by Rigaku Corporation, attachment device: rotational sample table, X-ray source: CuKα, output: 40 kV, 370 mA, detector: scintillation counter).

Examples of a method of measuring the degree of orientation F of the first piezoelectric material are as described in examples described later.

"One direction" refers to a direction in which the first piezoelectric material is wound around the conductor from the near side to the far side when viewing the piezoelectric substrate of the present embodiment from one axial direction end of the conductor. Specifically, "one direction" refers to a right direction (right-handed, i.e., clockwise) or a left direction (left-handed, i.e., counterclockwise).

Due to including such a configuration, the piezoelectric substrate of the present embodiment is excellent in piezoelectric sensitivity and also excellent in the piezoelectric output stability.

More specifically, the piezoelectric substrate of the present embodiment exhibits piezoelectric properties due to the first piezoelectric material including the helical chiral polymer (A), the lengthwise direction of the first piezoelectric material and the principal orientation direction of the helical chiral polymer (A) being substantially parallel to each other, and the degree of orientation F of the first piezoelectric material being from 0.5 up to but not including 1.0.

Moreover, the piezoelectric substrate of the present embodiment has a configuration in which the first piezoelectric material is helically wound in one direction around the conductor.

In the piezoelectric substrate of the present embodiment, due to the first piezoelectric material being arranged in the manner described above, a shear force is applied to the helical chiral polymer (A) when tension (stress) has been applied to the piezoelectric substrate in the lengthwise direction, and polarization of the helical chiral polymer (A) occurs along the radial directions of the piezoelectric substrate. When the helically wound first piezoelectric material is regarded as being an aggregate body of micro regions micronized to the extent that they approximate to flat planes along the lengthwise direction of the first piezoelectric material, application to the helical chiral polymer of a shear force caused by tension (stress) acting on the flat planes configuring the micro regions results in the direction of such polarization substantially coinciding with the direction of an electric field generated due to a piezoelectric stress constant $d_{14}$.

Specifically, in polylactic acids for example, in the case of a homopolymer (PLLA) of L-lactic acid having a molecular structure including a left-handed helical structure, application of tension (stress) to a left-handed helically wound structure, in which a first piezoelectric material having a lengthwise direction substantially parallel to the principal orientation direction of the PLLA has been wound around a conductor in a left-handed manner, results in generation of an electric field (polarization) parallel to radial directions and acting in directions from the center of a circle of a circular cross-section perpendicular to the tension toward the outside. Conversely, when tension (stress) has been applied to a right-handed helically wound structure, in which a first piezoelectric material having a lengthwise direction substantially parallel to the principal orientation direction of the PLLA has been wound around a conductor in a right-handed manner, this results in generation of an electric field (polarization) parallel to radial directions, but acting in directions from the outside of a circle of a circular cross-section perpendicular to the tension toward the center thereof.

Moreover, for example, in the case of a homopolymer (PDLA) of D-lactic acid having a molecular structure including a right-handed helical structure, application of tension (stress) to a left-handed helically wound structure, in which a first piezoelectric material having a lengthwise direction substantially parallel to the principal orientation direction of the PDLA has been wound around a conductor in a left-handed manner, results in generation of an electric field (polarization) parallel to radial directions and acting in directions from the outside of a circle of a circular cross-section perpendicular to the tension, toward the center thereof. Conversely, when tension (stress) is applied to a right-handed helically wound structure, in which a first piezoelectric material having a lengthwise direction substantially parallel to the principal orientation direction of the PDLA has been wound around a conductor in a right-handed manner, this results in generation of an electric field (polarization) parallel to radial directions, but acting in directions from the center of a circle of a circular cross-section perpendicular to the tension, toward the outside.

As a result, when tension has been applied to the piezoelectric substrate in the lengthwise direction, a voltage signal proportional to this tension is thought to be effectively detectable due to respective potential differences proportional to the tension being generated at each site of the helically arranged first piezoelectric material in a state of phase alignment.

Therefore, a piezoelectric substrate that is excellent in piezoelectric sensitivity and also excellent in the piezoelectric output stability can be obtained according to the piezoelectric substrate of the present embodiment.

In particular, the stability of piezoelectric sensitivity and the piezoelectric output stability (stability with respect to time or change in temperature) in a piezoelectric substrate using a non-pyroelectric polylactic acid-based polymer as the helical chiral polymer (A) are improved in comparison to those of a piezoelectric substrate using PVDF that has pyroelectric properties.

In the piezoelectric unit provided with a fiber having piezoelectric properties described in JP-A No. 2008-146528, the direction in which the fiber having piezoelectric properties is wound around a conductive fiber is not limited therein, and both origin and direction of force configuring a shear force are different from those of the piezoelectric substrate of the present embodiment. Piezoelectric sensitivity is accordingly thought to be insufficient due to polarization not occurring along the radial directions of the piezoelectric unit. Namely, polarization does not occur in the direction of an electric field generated due to a piezoelectric stress constant $d_{14}$, even in cases in which tension is applied to the piezoelectric unit described in JP-A No. 2008-146528.

The lengthwise direction of the first piezoelectric material and the principal orientation direction of the helical chiral polymer (A) being substantially parallel to each other is advantageous from the perspective of the first piezoelectric material being strong to tension in the lengthwise direction (i.e., has excellent tensile strength in the lengthwise direction). The first piezoelectric material is accordingly not liable to break even when being helically wound in one direction around the conductor.

In addition, the lengthwise direction of the first piezoelectric material and the principal orientation direction of the helical chiral polymer (A) being substantially parallel to each other is also advantageous from the perspective of ease of manufacture when, for example, a stretched piezoelectric film is slit to obtain the first piezoelectric material (for example, a slit ribbon thereof).

Herein, "substantially parallel" indicates that an angle formed between two line segments is from 0° up to but not including 30° (preferably from 0° to 22.5°, more preferably from 0° to 10°, still more preferably from 0° to 5°, and particularly preferably from 0° to 3°).

Herein, the principal orientation direction of the helical chiral polymer (A) means the main orientation direction of the helical chiral polymer (A). The principal orientation direction of the helical chiral polymer (A) can be confirmed by measuring the degree of orientation F of the first piezoelectric material.

In cases in which a raw material is melted and spun before stretching to produce the first piezoelectric material, the principal orientation direction of the helical chiral polymer (A) in the produced first piezoelectric material means the principal stretching direction. The principal stretching direction refers to the direction in which stretching is performed.

Likewise, in cases in which a film is stretched, and slits are made in the stretched film to produce the first piezoelectric material, the principal orientation direction of the helical chiral polymer (A) in the produced first piezoelectric material means a principal stretching direction. The principal stretching direction refers here to the stretching direction in cases of monoaxial stretching, or refers here to the stretching direction having the higher stretching ratio in cases of biaxial stretching.

A first embodiment of the piezoelectric substrate in the present disclosure will be described in detail below.
(Piezoelectric Substrate of First Embodiment)

In the piezoelectric substrate of the first embodiment, the elongate conductor is preferably an inner conductor, and the elongate first piezoelectric material is preferably helically wound in one direction around the outer peripheral surface of the inner conductor.

Utilizing the inner conductor as the conductor facilitates the helical arrangement of the first piezoelectric material in one direction while maintaining the first piezoelectric material at a helix angle β with respect to the axial direction of the inner conductor.

"Helix angle β" means here an angle formed between the axial direction of the conductor and the arrangement direction of the first piezoelectric material with respect to the axial direction of the conductor (the lengthwise direction of the first piezoelectric material).

This facilitates the generation of polarization of the helical chiral polymer (A) along the radial directions of the piezoelectric substrate when, for example, tension is applied in the lengthwise direction of the piezoelectric substrate. As a result, a voltage signal (charge signal) proportional to the tension is effectively detected as an electrical characteristic.

In addition, a piezoelectric substrate configured as described above has the same structure as the internal structure provided in a coaxial cable (i.e. an inner conductor and a dielectric body). A structure that has high electromagnetic shielding properties and is resistant to noise is accordingly obtained when, for example, the piezoelectric substrate described above is applied to a coaxial cable.

The piezoelectric substrate of the first embodiment preferably further includes an elongate second piezoelectric material helically wound in a direction different from the one direction.

In addition, preferably the second piezoelectric material includes an optically active helical chiral polymer (A), the lengthwise direction of the second piezoelectric material and the principal orientation direction of the helical chiral polymer (A) included in the second piezoelectric material are substantially parallel to each other, the degree of orientation F of the second piezoelectric material, determined from X-ray diffraction measurement by Formula (a), is in a range of from 0.5 up to but not including 1.0, and the chirality of the helical chiral polymer (A) included in the first piezoelectric material and the chirality of the helical chiral polymer (A) included in the second piezoelectric material differ from each other.

Polarization thereby occurs in both the helical chiral polymer (A) included in the first piezoelectric material and the helical chiral polymer (A) included in the second piezoelectric material when, for example, tension has been applied in the lengthwise direction of the piezoelectric substrate. Each of these polarization directions is along the radial directions of the piezoelectric substrate.

As a result, a voltage signal (charge signal) proportional to the tension is more effectively detected. Accordingly, piezoelectric sensitivity and piezoelectric output stability are further improved.

In particular, in cases in which the piezoelectric substrate of the first embodiment includes a first outer conductor and a piezoelectric material formed into a double-layer structure that includes the first piezoelectric material and the second piezoelectric material, the first piezoelectric material and the second piezoelectric material can be brought into close contact with the inner conductor and the first outer conductor so as to form few voids therebetween. This facilitates efficient transmission of an electric field generated by tension to an electrode. Such a form of the piezoelectric material is accordingly well suited to achieving a sensor of higher sensitivity.

From the viewpoint of improving piezoelectric sensitivity and piezoelectric output stability, the piezoelectric substrate of the first embodiment preferably further includes a first insulator helically wound around the outer peripheral surface of the inner conductor, and the first insulator is preferably arranged on the opposite side from the inner conductor as viewed from the first piezoelectric material.

For example, in cases in which the piezoelectric substrate of the first embodiment includes a first outer conductor, gaps are readily formed in the wound first piezoelectric material if the piezoelectric substrate is repeatedly bent or the piezoelectric substrate is bent at a small curvature radius, giving rise to the possibility of the inner conductor and the first outer conductor electrically short-circuiting. Arranging the first insulator in such cases, however, enables the inner conductor and the first outer conductor to be more reliably electrically isolated from each other. This also enables high reliability to be achieved in applications employing a bent piezoelectric substrate.

Preferably the piezoelectric substrate of the first embodiment further includes an elongate second piezoelectric material wound in a direction different from the one direction. Herein, the second piezoelectric material includes an optically active helical chiral polymer (A), a lengthwise direction of the second piezoelectric material and a principal orientation direction of the helical chiral polymer (A) included in the second piezoelectric material are substantially parallel to each other, a degree of orientation F of the second piezoelectric material, determined from X-ray diffraction measurement by Formula (a), is in a range of from 0.5 up to but not including 1.0, the first piezoelectric material and the second piezoelectric material alternately intersect each other to form a braided structure, and a chirality of the helical chiral polymer (A) included in the first piezoelectric material and a chirality of the helical chiral polymer (A) included in the second piezoelectric material differ from each other.

Polarization thereby accordingly occurs in both the helical chiral polymer (A) included in the first piezoelectric material and the helical chiral polymer (A) included in the second piezoelectric material when, for example, tension has been applied in the lengthwise direction of the piezoelectric substrate. Each of these polarization directions is along the radial directions of the piezoelectric substrate.

A voltage signal proportional to the tension is thereby more effectively detected. As a result the piezoelectric sensitivity and piezoelectric output stability are further improved.

In particular, in cases in which the piezoelectric substrate of the first embodiment includes a first outer conductor and a piezoelectric material including the first piezoelectric material and the second piezoelectric material formed into a braided structure, an appropriate level of voids is formed between the first piezoelectric material and the second piezoelectric material. The voids accordingly absorb deformation when a force acts on the piezoelectric material to cause bending deformation therein, facilitating supple bending deformation of the piezoelectric substrate. This thereby enables the piezoelectric substrate of the first embodiment to be suitably used, for example, as a configuration member to be conformed to a three-dimensional plane, such as in a wearable product.

From the viewpoint of improving piezoelectric sensitivity and piezoelectric output stability, the piezoelectric substrate of the first embodiment preferably further includes a first insulator wound around the outer peripheral surface of the inner conductor, wherein the first piezoelectric material and the first insulator alternately intersect each other to form a braided structure.

This makes it easier to maintain a state in which the first piezoelectric material is wound around the inner conductor in one direction when the piezoelectric substrate is undergoing bending deformation. There are preferably no gaps between the first piezoelectric material and the first insulator in the braided structure of such an aspect from the viewpoint that this facilitates the application of tension to the first piezoelectric material.

From the viewpoint of improving piezoelectric sensitivity and piezoelectric output stability, in the piezoelectric substrate of the first embodiment, the first piezoelectric material is preferably wound so as to maintain an angle of from 15° to 75° (45°±30°), and more preferably wound so as to maintain an angle of from 35° to 55° (45°±10°), with respect to the axial direction of the inner conductor.

From the viewpoint of improving piezoelectric sensitivity and piezoelectric output stability, in the piezoelectric substrate of the first embodiment, the first piezoelectric material preferably has a fiber shape that includes a single or plural bundles, and the major axis diameter of a cross-section of the first piezoelectric material is preferably from 0.0001 mm to 10 mm, more preferably from 0.001 mm to 5 mm, and still more preferably from 0.002 mm to 1 mm.

"Major axis diameter of cross-section" is equivalent to "diameter" in cases in which a cross-section of the first piezoelectric material (preferably a fibrous piezoelectric material) has a circular profile.

In cases in which a cross-section of the first piezoelectric material has an irregular profile, the "major axis diameter of cross-section" is the longest width from out of such cross-sectional widths.

In cases in which the first piezoelectric material is a piezoelectric material configured from plural bundles, the "major axis diameter of cross-section" is the major axis diameter of a cross-section of the piezoelectric material configured from the plural bundles.

From the viewpoint of improving the piezoelectric sensitivity and piezoelectric output stability in the piezoelectric substrate of the present embodiment (for example, in the piezoelectric substrate of the first embodiment), the first piezoelectric material preferably has an elongate flat plate shape. The thickness of the first piezoelectric material is from 0.001 mm to 0.2 mm, the width of the first piezoelectric material is from 0.1 mm to 30 mm, and a ratio of the width of the first piezoelectric material to the thickness of the first piezoelectric material is 2 or more.

The dimensions (thickness, width, and ratios (width/thickness, and length/width)) of the first piezoelectric material having an elongate flat plate shape (hereinafter also referred to as "elongate-flat-plate-shaped piezoelectric material") will be described in more detail below.

The first piezoelectric material preferably has a thickness of from 0.001 mm to 0.2 mm.

A thickness of 0.001 mm or more secures the strength of the elongate-flat-plate-shaped piezoelectric material to be secured. This is also excellent in terms of ease of production of the elongate-flat-plate-shaped piezoelectric material.

A thickness of 0.2 mm or less results improves the degrees of freedom for deformation (flexibility) of the elongate-flat-plate-shaped piezoelectric material in the thickness direction.

In addition, the width of the first piezoelectric material is preferably from 0.1 mm to 30 mm.

A width of 0.1 mm or more secures the strength of the first piezoelectric material (elongate-flat-plate-shaped piezoelectric material). This is also excellent in terms of ease of production of the elongate-flat-plate-shaped piezoelectric material (for example, in terms of the ease of production in a slitting process, described later).

A width of 30 mm or less results in improvement in the degrees of freedom for deformation (flexibility) of the elongate-flat-plate-shaped piezoelectric material.

In addition, a ratio of the width of the first piezoelectric material to the thickness of the first piezoelectric material (hereinafter also referred to as "ratio (width/thickness)") is preferably 2 or more.

When the ratio (width/thickness) is 2 or more, the principal faces are clearly defined, thereby facilitating formation of an electrode layer (for example, an outer conductor) having a uniform orientation over the lengthwise direction of the first piezoelectric material (elongate-flat-plate-shaped piezoelectric material). For example, an outer conductor is easily formed on at least one of the principal faces. This is accordingly excellent in terms of piezoelectric sensitivity, and also excellent in terms of the stability of the piezoelectric sensitivity.

The width of the first piezoelectric material is more preferably from 0.5 mm to 15 mm.

When the width is 0.5 mm or more, there is a greater improvement in the strength of the first piezoelectric material (elongate-flat-plate-shaped piezoelectric material). In addition, twisting of the elongate-flat-plate-shaped piezoelectric material can also be better inhibited, thereby enabling the piezoelectric sensitivity and the stability thereof to be further improved.

A width of 15 mm or less results in a greater improvement in the degrees of freedom for deformation (flexibility) of the elongate-flat-plate-shaped piezoelectric material.

The ratio of the length to the width (hereinafter also referred to as "ratio (length/width)") of the first piezoelectric material is preferably 10 or more.

When the ratio (length/width) is 10 or more, there is a greater improvement in the degrees of freedom for deformation (flexibility) of the first piezoelectric material (elongate-flat-plate-shaped piezoelectric material). In addition, piezoelectric properties can be imparted more extensively to a piezoelectric device (such as a piezoelectric textile or a piezoelectric fabric) in which elongate-flat-plate-shaped piezoelectric materials are appropriately employed.

In the piezoelectric substrate of the present embodiment, a functional layer is preferably arranged on at least one principal face of the first piezoelectric material from the viewpoint of improving the piezoelectric sensitivity and piezoelectric output stability in cases in which the first piezoelectric material has an elongate flat plate shape.

The functional layer preferably includes at least one of an adhesion facilitation layer, a hard coat layer, an antistatic layer, an antiblock layer, a protective layer, or an electrode layer.

This further facilitates application to, for example, a piezoelectric device (such as a piezoelectric textile or a piezoelectric fabric), a force sensor, an actuator, or a biodata acquisition device.

The functional layer preferably includes an electrode layer.

This enables a connection between the first outer conductor and the conductor (preferably an inner conductor) to be more easily made in cases in which the piezoelectric substrate is being employed as one of the configuration elements of, for example, a piezoelectric device (such as a piezoelectric textile or a piezoelectric fabric), a force sensor, an actuator, or a biodata acquisition device. This facilitates detection of a voltage signal corresponding to tension when tension has been applied to the piezoelectric substrate of the present embodiment.

In the piezoelectric substrate of the present embodiment, preferably at least one surface layer of a layered body including the first piezoelectric material and the functional layer is the electrode layer.

This enables a connection between the first outer conductor or the conductor (preferably an inner conductor) and the layered body to be more easily made in cases in which the piezoelectric substrate is being employed as one of the configuration elements of, for example, a piezoelectric device (such as a piezoelectric textile or a piezoelectric fabric), a force sensor, an actuator, or a biodata acquisition device. This facilitates detection of a voltage signal corresponding to tension when tension has been applied to the piezoelectric substrate of the present embodiment.

In the piezoelectric substrate of the present embodiment, the conductor is preferably a tinsel wire.

The form of the tinsel wire has a structure in which a rolled copper foil is helically wound around a fiber. Employing copper that has a high electric conductivity enables the output impedance to be decreased. This facilitates detection of a voltage signal corresponding to tension when tension has been applied to the piezoelectric substrate of the present embodiment. As a result, piezoelectric sensitivity and piezoelectric output stability are further improved.

The piezoelectric substrate of the present embodiment preferably includes an adhesive layer between the conductor and the first piezoelectric material.

The relative position of the conductor and the first piezoelectric material is thereby inhibited from shifting, facilitating application of tension to the first piezoelectric material, and facilitating application of a shear stress to the helical chiral polymer (A) included in the first piezoelectric material. This enables a voltage output proportional to the tension to be effectively detected from the conductor (preferably a signal line conductor). The inclusion of the adhesive layer results in a further increase in the absolute value of the amount of generated charge per unit tensile force.

In the piezoelectric substrate of the present embodiment, the helical chiral polymer (A) included in the first piezoelectric material is preferably a polylactic acid-based polymer having a main chain including a repeating unit represented by the following Formula (1), from the viewpoint of further improving piezoelectric properties.

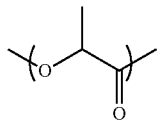
(1)

In the piezoelectric substrate of the present embodiment, the helical chiral polymer (A) included in the first piezoelectric material preferably has an optical purity of 95.00% ee or more, from the viewpoint of further improving piezoelectric properties.

In the piezoelectric substrate of the present embodiment, the helical chiral polymer (A) included in the first piezoelectric material is preferably D-form or L-form, from the viewpoint of further improving piezoelectric properties.

In the piezoelectric substrate of the present embodiment, the content of the helical chiral polymer (A) included in the first piezoelectric material is preferably 80% by mass or more with respect to the total amount of the first piezoelectric material, from the viewpoint of further improving piezoelectric properties.

The piezoelectric substrate of the present embodiment preferably further includes a first outer conductor at an outer periphery.

"Outer periphery" here means an outer peripheral portion of the piezoelectric substrate.

This enables electrostatic shielding to be achieved, and for fluctuations in the voltage of the conductor (preferably an inner conductor) arising from the effects of external static electricity to be suppressed.

The piezoelectric substrate of the present embodiment preferably further includes a second insulator at the outer periphery of the first outer conductor.

Due to the piezoelectric substrate of the present embodiment including the second insulator, the ingress of liquids such as water or sweat, and the ingress of dust or the like, from outside can be suppressed. This enables generation of leakage current between the conductor (preferably an inner conductor) and the outer conductor, caused by water, sweat, dust, or the like, to be suppressed. As a result, this enables a stable output to be achieved that is robust to various environmental changes and is not liable to fluctuate in sensitivity, in cases in which the piezoelectric substrate is used as one of the configuration elements of, for example, a piezoelectric device (such as a piezoelectric textile or a piezoelectric fabric), a force sensor, an actuator, or a biodata acquisition device.

A specific aspect A of the piezoelectric substrate according to the first embodiment will be described below, with reference to the drawings.

(Specific Aspect A)

Figure 6A:
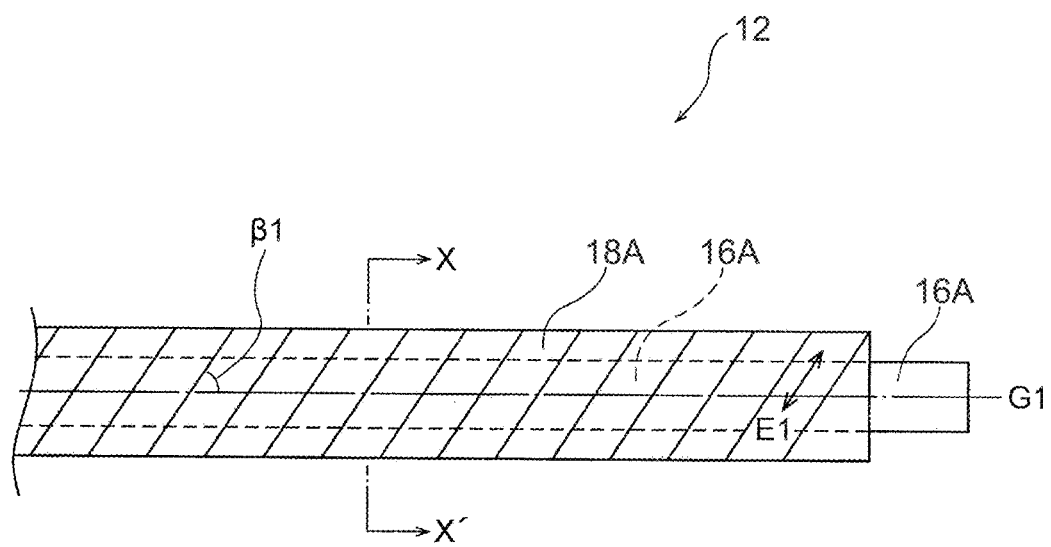
FIG. 6A is a side view illustrating a specific aspect A of a piezoelectric substrate according to the first embodiment.
Figure 6B:
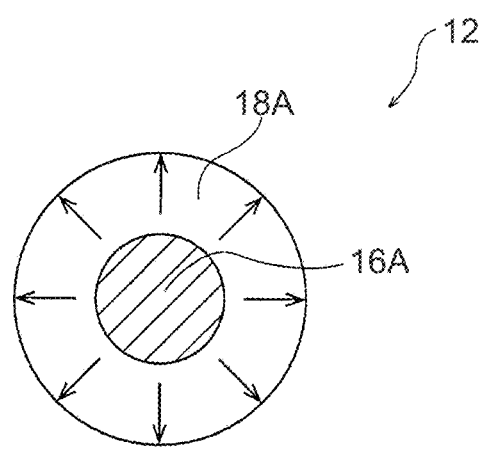
FIG. 6B is a cross-section illustrating the specific aspect A of the piezoelectric substrate according to the first embodiment (taken along the line X-X' of FIG. 6A).

FIG. 6A is a side view illustrating the specific aspect A of the piezoelectric substrate according to the first embodiment. FIG. 6B is a cross-section taken along the line X-X' of FIG. 6A.

A piezoelectric substrate 12 of the specific aspect A includes an elongate inner conductor 16A as the conductor, an elongate first piezoelectric material 18A, and an adhesive layer (not illustrated) interposed between the inner conductor 16A and the first piezoelectric material 18A.

As illustrated in FIG. 6A, the first piezoelectric material 18A is helically wound at a helix angle β1 around the outer peripheral surface of the inner conductor 16A in one direction from one end to the other end thereof so that there is no gap present therebetween.

"Helix angle β1" means an angle formed between an axial direction G1 of the inner conductor 16A and the arrangement direction of the first piezoelectric material 18A with respect to the axial direction of the inner conductor 16A.

In the specific aspect A, the first piezoelectric material 18A is wound in a left-handed manner around the inner conductor 16A. Specifically, the first piezoelectric material 18A is wound in a left-handed manner from the near side to the far side of the inner conductor 16A when the piezoelectric substrate 12 is viewed from one axial direction end of the inner conductor 16A (at the right end side in FIG. 6A).

In FIG. 6A, the principal orientation direction of the helical chiral polymer (A) included in the first piezoelectric material 18A is indicated by the double-headed arrow E1. In other words, the principal orientation direction of the helical chiral polymer (A) and the arrangement direction of the first piezoelectric material 18A (the lengthwise direction of the first piezoelectric material 18A) are substantially parallel to each other.

The adhesive layer (not illustrated) is interposed between the inner conductor 16A and the first piezoelectric material 18A. The piezoelectric substrate 12 of the specific aspect A is thereby configured so that the relative position of the first piezoelectric material 18A and the inner conductor 16A does not shift even when tension is applied to the piezoelectric substrate 12 in the lengthwise direction thereof.

The operation and advantageous effects of the piezoelectric substrate 12 of the specific aspect A will be described below.

For example, when tension is applied to the piezoelectric substrate 12 in the lengthwise direction thereof, a shear force is applied to the helical chiral polymer (A) included in the first piezoelectric material 18A, thereby polarizing the helical chiral polymer (A). The polarization of the helical chiral polymer (A) is thought to occur along the radial directions of the piezoelectric substrate 12, as indicated by the arrows in FIG. 6B, with the polarization occurring in-phase with each other. As a result, a voltage signal proportional to the tension is effectively detected.

Furthermore, in the piezoelectric substrate 12 of the specific aspect A, tension is more readily applied to the first piezoelectric material 18A due to the adhesive layer being interposed between the inner conductor 16A and the first piezoelectric material 18A.

Due to the above configuration, the piezoelectric substrate 12 of the specific aspect A is excellent in piezoelectric sensitivity and is excellent in piezoelectric output stability.

A specific aspect B of the piezoelectric substrate according to the first embodiment will now be described, with reference to the drawings. In the following description, configuration the same as the specific aspect A is appended with the same reference signs, and duplicate description is omitted thereof.

(Specific Aspect B)

Figure 7:
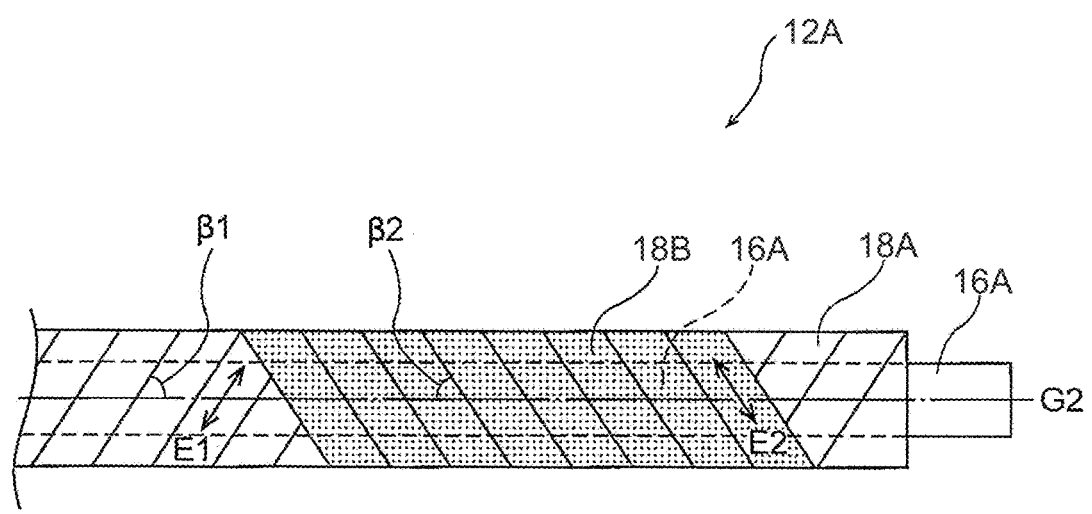
FIG. 7 is a side view illustrating a specific aspect B of a piezoelectric substrate according to the first embodiment.

FIG. 7 is a side view illustrating the specific aspect B of the piezoelectric substrate according to the first embodiment.

A piezoelectric substrate 12A of the specific aspect B differs from the piezoelectric substrate 12 of the first aspect in including an elongate second piezoelectric material 18B.

The chirality of the helical chiral polymer (A) included in the first piezoelectric material 18A and the chirality of a helical chiral polymer (A) included in the second piezoelectric material 18B differ from each other.

Similarly to in the specific aspect A, the first piezoelectric material 18A is helically wound at a helix angle β1 around the outer peripheral surface of the inner conductor 16A in one direction from one end to the other end so that there are no gaps present therebetween.

However, the second piezoelectric material 18B is helically wound in the reverse direction to the direction of winding the first piezoelectric material 18A at a helix angle β2, which is substantially the same angle as the helix angle β1, around the outer peripheral surface of the first piezoelectric material 18A, as illustrated in FIG. 7.

"Helix angle β2" is defined in a similar manner to the helix angle β1 described above.

The "reverse direction to the direction of winding of the first piezoelectric material 18A" in the specific aspect B refers here to being right-handed. In other words, the second piezoelectric material 18B is wound in a right-handed manner from the near side to the far side of the inner conductor 16A when the piezoelectric substrate 12A is viewed from one end in an axial direction G2 of the inner conductor 16A (at the right end side in FIG. 7).

In FIG. 7, the principal orientation direction of the helical chiral polymer (A) included in the second piezoelectric material 18B is indicated by the double-headed arrow E2. In other words, the principal orientation direction of the helical chiral polymer (A) included in the second piezoelectric material 18B and the arrangement direction of the second piezoelectric material 18B (the lengthwise direction of the second piezoelectric material 18B) are substantially parallel to each other.

The operation of the piezoelectric substrate 12A of the specific aspect B will be described below.

For example, when tension is applied to the piezoelectric substrate 12A in the lengthwise direction thereof, a shear stress is applied to both the helical chiral polymer (A) included in the first piezoelectric material 18A and the helical chiral polymer (A) included in second piezoelectric material 18B, and polarization accordingly occurs therein. Each of the polarization directions is along the radial directions of the piezoelectric substrate 12A. A voltage signal proportional to the tension is accordingly effectively detected.

Due to the above configuration, the piezoelectric substrate 12A of the specific aspect B achieves greater improvements in the piezoelectric sensitivity and piezoelectric output stability.

In particular, in cases in which the piezoelectric substrate 12A of the specific aspect B includes an outer conductor, due to the piezoelectric material including the first piezoelectric material and the second piezoelectric material formed in a double-layer structure, this enables the first piezoelectric material and the second piezoelectric material to be brought into close contact with the inner conductor and the outer conductor so as to form few voids therebetween. This facilitates efficient transmission of an electric field generated by tension to an electrode. Such a form of the piezoelectric material is accordingly well suited to achieving a sensor of higher sensitivity.

A specific aspect C of the piezoelectric substrate according to the first embodiment will now be described, with reference to the drawings. In the following description, the same reference signs are appended to the same configuration as that in the specific aspect A and the specific aspect B, and duplicate explanation thereof will be omitted.

(Specific Aspect C)

Figure 8:
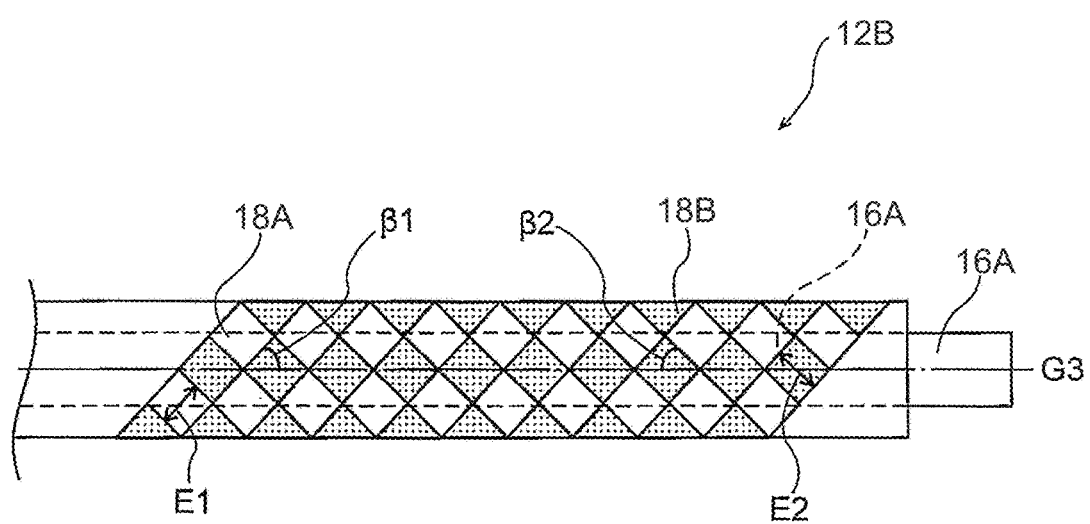
FIG. 8 is a side view illustrating a specific aspect C of a piezoelectric substrate according to the first embodiment.

FIG. 8 is a side view illustrating a specific aspect C of the piezoelectric substrate according to the first embodiment.

A piezoelectric substrate 12B of the specific aspect C differs from the piezoelectric substrate 12A of the specific aspect B in that a first piezoelectric material 18A and a second piezoelectric material 18B alternately intersect each other to form a braided structure.

The chirality of a helical chiral polymer (A) included in the first piezoelectric material 18A and the chirality of a helical chiral polymer (A) included in the second piezoelectric material 18B differ from each other.

As illustrated in FIG. 8, in the piezoelectric substrate 12B of the specific aspect C, the first piezoelectric material 18A is helically wound in a left-handed manner at a helix angle 131 with respect to an axial direction G3 of an inner conductor 16A, and the second piezoelectric material 18B is helically wound in a right-handed manner at a helix angle β2 with respect thereto. The first piezoelectric material 18A and the second piezoelectric material 18B alternately intersect each other.

In the braided structure illustrated in FIG. 8, the principal orientation direction (double-headed arrow E1) of the helical chiral polymer (A) included in first piezoelectric material 18A and the arrangement direction of the first piezoelectric material 18A are substantially parallel to each other. Similarly, the principal orientation direction (double-headed arrow E2) of the helical chiral polymer (A) included in the second piezoelectric material 18B and the arrangement direction of the second piezoelectric material 18B are substantially parallel to each other.

The operation and advantageous effects of the piezoelectric substrate 12B of the specific aspect C will be described below.

Similarly to in the specific aspect B, polarization occurs in both of the helical chiral polymer (A) included in the first piezoelectric material 18A and the helical chiral polymer (A) included in second piezoelectric material 18B when, for example, tension is applied to the piezoelectric substrate 12B in the lengthwise direction thereof. Each of the polarization directions is along the radial directions of the piezoelectric substrate 12B. As a result, a voltage signal proportional to the tension is effectively detected.

Due to the above configuration, the piezoelectric substrate 12B of the specific aspect C results achieves a greater improvement in piezoelectric sensitivity and piezoelectric output stability.

In particular, in cases in which the piezoelectric substrate 12B of the specific aspect C includes an outer conductor, when tension has been applied in the lengthwise direction of the piezoelectric substrate 12B, a shear stress is applied to the left-hand-wound first piezoelectric material and the right-hand-wound second piezoelectric material forming the braided structure. The polarization directions thereof are aligned with each other, a volume fraction contributing to the piezoelectric performance of the insulator (i.e., the first piezoelectric material and the second piezoelectric material) between the inner conductor and the outer conductor is increased, and the piezoelectric performance is therefore further improved. This thereby enables the piezoelectric substrate 12B of the specific aspect C to be suitably used, for example, as a configuration member to be conformed to a three-dimensional plane, such as in a wearable product.

The conductor, the first piezoelectric material, and the like included in the piezoelectric substrate of the present embodiment will be described below.

<Conductor>

The piezoelectric substrate of the present embodiment includes an elongate conductor.

The conductor (for example, an inner conductor) in the present embodiment is preferably a signal line conductor.

The signal line conductor refers to a conductor for efficiently detecting an electrical signal from the first piezoelectric material or the second piezoelectric material. Specifically, the signal line conductor is a conductor for detecting a voltage signal (charge signal) corresponding to tension applied when tension has been applied to the piezoelectric substrate of the present embodiment.

The conductor is preferably a good electrical conductor. Examples that may be employed as the conductor include a copper wire, an aluminum wire, an SUS wire, a metal wire coated with an insulating covering layer, a carbon fiber, a resin fiber integrated with a carbon fiber, a tinsel wire, an organic conductive material, and the like. The tinsel wire refers to a wire formed by spirally winding a copper foil around a fiber. Among such conductors, a tinsel wire and a carbon fiber are preferred from the viewpoint of improving piezoelectric sensitivity and piezoelectric output stability, and imparting high flexibility.

In particular, a tinsel wire is preferably used in an application having low electrical resistivity and requiring flexibility and pliability (for example, an application such as a wearable sensor built into clothing).

A carbon fiber is preferably used in processing applications to produce textiles or fabrics that demand very high flexibility and suppleness (for example, a piezoelectric textile, a piezoelectric fabric, or a piezoelectric sensor (a textile-form piezoelectric sensor or a fabric-form piezoelectric sensor)).

Suppleness and high flexibility are demanded in cases in which the piezoelectric substrate of the present embodiment is used as a fiber to be processed into a piezoelectric textile or a piezoelectric fabric. A yarn-form or fibrous signal line conductor is preferred in such applications. A piezoelectric substrate including a yarn-form or fibrous signal line conductor has high flexibility, and is therefore well suited to processing with a weaving machine or a knitting machine.

<First Piezoelectric Material>

The piezoelectric substrate of the present embodiment includes the elongate first piezoelectric material.

The first piezoelectric material is a piezoelectric material including an optically active helical chiral polymer (A).

(Helical Chiral Polymer (A))

The first piezoelectric material in the present embodiment includes an optically active helical chiral polymer (A).

Here, "optically active helical chiral polymer" refers to a polymer having a helical molecular structure and having molecular optical activity.

Examples of the helical chiral polymer (A) include polypeptides, cellulose derivatives, polylactic acid-based polymers, polypropylene oxide, and poly(β-hydroxybutyric acid).

Examples of the polypeptides include poly(glutaric acid γ-benzyl) and poly(glutaric acid γ-methyl).

Examples of the cellulose derivatives include cellulose acetate and cyanoethyl cellulose.

From the viewpoint of improving the piezoelectric properties of the first piezoelectric material, the helical chiral polymer (A) preferably has an optical purity of 95.00% ee or more, more preferably 96.00% ee or more, still more preferably 99.00% ee or more, and even more preferably 99.99% ee or more. The helical chiral polymer (A) desirably has an optical purity of 100.00% ee. Adopting an optical purity of the helical chiral polymer (A) in the above ranges raises the ease-of-packing of polymer crystals that exhibit piezoelectric properties, and this is thought to consequently result in improved piezoelectric properties.

The optical purity of the helical chiral polymer (A) referred to here is a value calculated by the following Formula.

Optical purity (% ee)=100×|L-form amount−D-form amount|/(L-form amount+D-form amount)

In other words, the optical purity of the helical chiral polymer (A) is a value obtained by multiplying by "100" (by obtaining the product by 100 of) "a numerical value obtained by dividing (by obtaining the quotient of) 'the difference (absolute value) between the amount (mass %) of helical chiral polymer (A) in L-form and the amount (mass %) of helical chiral polymer (A) in D-form' by 'the total amount of the amount (mass %) of helical chiral polymer (A) in L-form and the amount (mass %) of helical chiral polymer (A) in D-form'.

Values obtained by a high performance liquid chromatography (HPLC) method are employed for the amount (mass %) of helical chiral polymer (A) in L-form and the amount (mass %) of helical chiral polymer (A) in D-form. The details of specific measurement will be described later.

A polymer having a main chain including a repeating unit represented by the following Formula (1) is preferably employed as the helical chiral polymer (A) from the viewpoint of increasing the optical purity and improving the piezoelectric properties.

(1)

Examples of the polymer having a main chain including a repeating unit represented by the above Formula (1) include a polylactic acid-based polymer.

Polylactic acid-based polymer refers here to "polylactic acid (a polymer consisting of a repeating unit derived from a monomer selected from L-lactic acid or D-lactic acid)", "a copolymer of L-lactic acid or D-lactic acid and a compound copolymerizable with the L-lactic acid or D-lactic acid", or a mixture thereof.

Among such polylactic acid-based polymers, polylactic acid is preferred, and a homopolymer (PLLA, also simply referred to as "L-form") of L-lactic acid or a homopolymer (PDLA, also simply referred to as "D-form") of D-lactic acid is most preferred.

Polylactic acid is a polymer obtained by polymerizing lactic acid by ester bonding so as to connect together in a long polymer.

Known methods capable of producing polylactic acid include a lactide method involving lactide, a direct polymerization method in which lactic acid is heated in a solvent under reduced pressure so as to be polymerized while removing water, and the like.

Examples of the polylactic acid include a homopolymer of L-lactic acid, a homopolymer of D-lactic acid, a block copolymer including a polymer of at least one of L-lactic acid or D-lactic acid, or a graft copolymer including a polymer of at least one of L-lactic acid or D-lactic acid.

Note that although the glass transition temperature of polylactic acid differs depending on the molecular weight and the degree of crystallization caused by elongation, it is in the region of from 50° C. to 70° C.

Examples of the "compound copolymerizable with L-lactic acid or D-lactic acid" include: a hydroxycarboxylic acid such as glycolic acid, dimethyl glycolic acid, 3-hydroxybutyric acid, 4-hydroxybutyric acid, 2-hydroxypropanoic acid, 3-hydroxypropanoic acid, 2-hydroxyvaleric acid, 3-hydroxyvaleric acid, 4-hydroxyvaleric acid, 5-hydroxyvaleric acid, 2-hydroxycaproic acid, 3-hydroxycaproic acid, 4-hydroxycaproic acid, 5-hydroxycaproic acid, 6-hydroxycaproic acid, 6-hydroxymethyl caproic acid, and mandelic acid; a cyclic ester such as glycolide, β-methyl-δ-valerolactone, γ-valerolactone, and ε-caprolactone; a polycarboxylic acid such as oxalic acid, malonic acid, succinic acid, glutaric acid, adipic acid, pimelic acid, azelaic acid, sebacic acid, undecanedioic acid, dodecanedioic acid, terephthalic acid, and an anhydride thereof a polyalcohol such as ethylene glycol, diethylene glycol, triethylene glycol, 1,2-propanediol, 1,3-propanediol, 1,3-butanediol, 1,4-butanediol, 2,3-butanediol, 1,5-pentanediol, 1,6-hexanediol, 1,9-nonanediol, 3-methyl-1,5-pentanediol, neopentyl glycol, tetramethylene glycol, and 1,4-hexanedimethanol; a polysaccharide such as cellulose; an aminocarboxylic acid such as α-amino acid; and the like.

Examples of the "copolymer of L-lactic acid or D-lactic acid and a compound copolymerizable with the L-lactic acid or the D-lactic acid" include a block copolymer or a graft copolymer having a polylactic acid sequence capable of forming a helical crystal.

The concentration of a copolymer component derived structure in the helical chiral polymer (A) is preferably 20 mol % or less.

For example, in cases in which the helical chiral polymer (A) is a polylactic acid-based polymer, the concentration of the copolymer component derived structure is preferably 20 mol % or less with respect to the total number of moles in the polylactic acid-based polymer of a lactic acid derived structure and a structure derived from the compound copolymerizable with lactic acid (copolymer component).

Examples of methods capable of producing the polylactic acid-based polymer include, for example: a method of obtaining the polymer by direct dehydration condensation of lactic acid, described in JP-A No. S59-096123 and JP-A No. H7-033861; a method of obtaining the polymer by ring-opening polymerization of lactide which is a cyclic dimer of lactic acid, described in U.S. Pat. Nos. 2,668,182 and 4,057,357; and the like.

Moreover, in order to achieve an optical purity of 95.00% ee or more in the polylactic acid-based polymer obtained by the above production methods, lactide having an optical purity improved by crystallization operations to an optical purity of 95.00% ee or more is preferably polymerized when, for example, a polylactic acid is produced by a lactide method.

—Weight Average Molecular Weight—

The weight average molecular weight (Mw) of the helical chiral polymer (A) is preferably from 50,000 to 1,000,000.

The mechanical strength of the first piezoelectric material is improved by making the Mw of the helical chiral polymer (A) 50,000 or more. The above Mw is preferably 100,000 or more, and is still more preferably 200,000 or more.

When obtaining the first piezoelectric material by molding (for example, extrusion molding or melt spinning), the moldability is improved by making the Mw of the helical chiral polymer (A) 1,000,000 or less. The Mw is preferably 800,000 or less, and is still more preferably 300,000 or less.

From the viewpoint of improving the strength of the first piezoelectric material, the molecular weight distribution (Mw/Mn) of the helical chiral polymer (A) is preferably from 1.1 to 5, and more preferably from 1.2 to 4. From 1.4 to 3 is still more preferable therefor.

The weight average molecular weight (Mw) and the molecular weight distribution (Mw/Mn) of the helical chiral polymer (A) refer to values measured using a gel permeation chromatograph (GPC). Mn here is the number-average molecular weight of the helical chiral polymer (A).

An example of a method of measuring Mw and Mw/Mn of the helical chiral polymer (A) using GPC will be described below.

—GPC Measurement Apparatus—

GPC-100, manufactured by Waters Corp.

—Column—

SHODEX LF-804, manufactured by Showa Denko K.K.

—Preparation of Sample—

The first piezoelectric material is dissolved in a solvent (for example, chloroform) at 40° C. to prepare a sample solution having a concentration of 1 mg/mL.

—Measurement Conditions—

0.1 mL of the sample solution is introduced into a column at a temperature of 40° C. and a flow rate of 1 mL/min using chloroform as a solvent.

The concentration of the sample in the sample solution separated by the column is measured by a differential refractometer.

A universal calibration curve is established based on a polystyrene standard sample, and the weight average molecular weight (Mw) and the molecular weight distribution (Mw/Mn) of the helical chiral polymer (A) are calculated.

A commercially available polylactic acid may be used as the polylactic acid-based polymer, serving as an example of the helical chiral polymer (A).

Examples of the commercially available product include PURASORB (PD, PL) manufactured by PURAC Inc., LACEA (H-100, H-400) manufactured by Mitsui Chemical Inc., and INGEO™ BIOPOLYMER manufactured by NatureWorks LLC.

In cases in which a polylactic acid-based polymer is used as the helical chiral polymer (A), the polylactic acid-based polymer is preferably produced by a lactide method or a direct polymerization method in order to achieve a weight average molecular weight (Mw) of the polylactic acid-based polymer of 50,000 or more.

The first piezoelectric material in the present embodiment may contain one kind of such a helical chiral polymer (A) as described above alone, or may contain two or more kinds thereof.

The content of the helical chiral polymer (A) in the first piezoelectric material in the present embodiment (total content when two or more kinds thereof) is preferably 80% by mass or more with respect to the total amount of the first piezoelectric material.

<Stabilizer>

The first piezoelectric material preferably further includes a stabilizer (B) having in one molecule one or more kinds of functional group selected from the group consisting of a carbodiimide group, an epoxy group, and an isocyanate group, and having a weight average molecular weight of from 200 to 60,000. This enables a moist heat resistance thereof to be further improved.

"Stabilizer (B)" described in the paragraphs 0039 to 0055 of WO 2013/054918 may be used as the stabilizer (B).

Examples of compounds including a carbodiimide group in one molecule (carbodiimide compound) that may be used as the stabilizer (B) include a monocarbodiimide compound, a polycarbodiimide compound, and a cyclic carbodiimide compound.

Preferred examples of the monocarbodiimide compound include dicyclohexylcarbodiimide and bis-2,6-diisopropylphenylcarbodiimide.

Polycarbodiimide compounds produced by various methods may be used as such polycarbodiimide compounds. Polycarbodiimide compounds produced by conventional methods for producing polycarbodiimides (for example as described in U.S. Pat. No. 2,941,956, Japanese Patent Publication (JP-B) No. S47-33279, and J. Org. Chem. 28, pp 2069-2075 (1963), Chemical Review 1981, Vol. 81 No. 4, pp 619-621) may be used therefor. Specifically, a carbodiimide compound described in Japanese Patent No. 4084953 may also be used therefor.

Examples of the polycarbodiimide compound include poly(4,4'-dicyclohexylmethanecarbodiimide), poly(N,N'-di-2,6-diisopropylphenylcarbodiimide), and poly(1,3,5-triisopropylphenylene-2,4-carbodiimide).

The cyclic carbodiimide compound can be synthesized by following, for example, a method described in JP-A No. 2011-256337.

A commercially available product may be used as the carbodiimide compound. Examples thereof include B2756 (trade name) manufactured by Tokyo Chemical Industry Co., Ltd., CARBODILITE LA-1 (trade name) manufactured by Nisshinbo Chemical Inc., and STABAXOL P, STABAXOL P400, and STABAXOL I (each being a trade name) manufactured by Rhein Chemie Rheinau Gmbh.

Examples of a compound (isocyanate compound) that may be used as the stabilizer (B) and includes an isocyanate group in one molecule include 3-(triethoxysilyl)propyl isocyanate, 2,4-tolylene diisocyanate, 2,6-tolylene diisocyanate, m-phenylene diisocyanate, p-phenylene diisocyanate, 4,4'-diphenylmethane diisocyanate, 2,4'-diphenylmethane diisocyanate, 2,2'-diphenylmethane diisocyanate, xylylene diisocyanate, hydrogenated xylylene diisocyanate, and isophorone diisocyanate.

Examples of a compound (epoxy compound) that may be used as the stabilizer (B) and includes an epoxy group in one molecule include phenylglycidyl ether, diethylene glycol diglycidyl ether, bisphenol-A-diglycidyl ether, hydrogenated bisphenol-A-diglycidyl ether, phenol novolac type epoxy resin, cresol novolac type epoxy resin, and epoxidized polybutadiene.

The weight average molecular weight of the stabilizer (B) is from 200 to 60,000 as described above, is more preferably from 200 to 30,000, and is still more preferably from 300 to 18,000.

Achieving a molecular weight within the above range results in the stabilizer (B) moving more easily, and in a moist heat resistance improvement effect being more effectively exhibited.

The weight average molecular weight of the stabilizer (B) is particularly preferably from 200 to 900. Note that a weight average molecular weight being from 200 to 900 is substantially the same as a number-average molecular weight being from 200 to 900. When the weight average molecular weight is from 200 to 900, the molecular weight distribution thereof is sometimes 1.0. A "weight average molecular weight of from 200 to 900" may also simply be referred to as a "molecular weight of from 200 to 900" in such cases.

In cases in which the first piezoelectric material contains the stabilizer (B), the first piezoelectric material may contain one kind of a stabilizer alone, or may contain two or more kinds thereof.

In cases in which the first piezoelectric material includes the stabilizer (B), the content of the stabilizer (B) is preferably from 0.01 parts by mass to 10 parts by mass, more preferably from 0.01 parts by mass to 5 parts by mass, still more preferably from 0.1 parts by mass to 3 parts by mass, and particularly preferably from 0.5 parts by mass to 2 parts by mass, with respect to 100 parts by mass of the helical chiral polymer (A).

Achieving a content as described above of 0.01 parts by mass or more results in a further improvement in moist heat resistance.

Achieving a content as described above of 10 parts by mass or less results in a deterioration of transparency being further suppressed.

An example of a preferred aspect of the stabilizer (B) includes an aspect in which a stabilizer (B1) including one or more kinds of functional group selected from the group consisting of a carbodiimide group, an epoxy group, and an isocyanate group and having a number-average molecular weight of from 200 to 900, is combined with a stabilizer (B2) including two or more functional groups in a molecule that are one or more kinds of functional group selected from the group consisting of a carbodiimide group, an epoxy group, and an isocyanate group and having a weight average molecular weight of from 1000 to 60,000. The weight average molecular weight of the stabilizer (B1) having a number-average molecular weight of from 200 to 900 is approximately from 200 to 900. The number-average molecular weight and the weight average molecular weight of the stabilizer (B1) are values which are substantially the same as each other.

In cases in which the stabilizer (B1) and the stabilizer (B2) are employed in combination as the stabilizer, a larger amount of stabilizer (B1) is preferably included therein from the viewpoint of improving transparency.

Specifically, with respect to 100 parts by mass of the stabilizer (B1), the amount of stabilizer (B2) is preferably in a range of from 10 parts by mass to 150 parts by mass from the viewpoint of achieving both transparency and moist heat resistance, and is more preferably in a range of from 50 parts by mass to 100 parts by mass.

Specific examples (stabilizers B-1 to B-3) of the stabilizer (B) are described below.

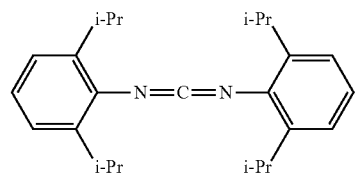

B-1

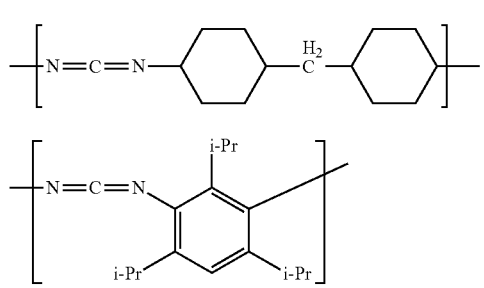

Compound names, commercially available products, and the like for the stabilizers B-1 to B-3 will be described below.

Stabilizer B-1: The compound name thereof is bis-2,6-diisopropylphenylcarbodiimide. The weight average molecular weight thereof (which is simply equivalent to "molecular weight" in this example) is 363. Examples of the commercially available products thereof include "STABAXOL I" manufactured by Rhein Chemie Rheinau Gmbh, and "B2756" manufactured by Tokyo Chemical Industry Co., Ltd.

Stabilizer B-2: The compound name thereof is poly(4,4'-dicyclohexylmethanecarbodiimide). Examples of the commercially available products thereof include "CARBODILITE LA-1" manufactured by Nisshinbo Chemical Inc., as a product having a weight average molecular weight of about 2000.

Stabilizer B-3: The compound name thereof is poly(1,3,5-triisopropylphenylene-2,4-carbodiimide). Examples of the commercially available products thereof include "STABAXOL P" manufactured by Rhein Chemie Rheinau Gmbh, as a product having a weight average molecular weight of about 3000. There is also "STABAXOL P400" manufactured by Rhein Chemie Rheinau Gmbh, as a product having a weight average molecular weight of 20,000.

<Other Components>

The first piezoelectric material may include another component, if necessary.

Examples of such other components include: known resins such as polyvinylidene fluoride, a polyethylene resin, and a polystyrene resin; known inorganic fillers such as silica, hydroxyapatite, and montmorillonite; known crystal nucleating agents such as phthalocyanine; and stabilizers other than the stabilizer (B).

Examples of such inorganic fillers and crystal nucleating agents include components described in the paragraphs 0057 to 0058 of WO 2013/054918.

(Degree of Orientation F)

The degree of orientation F of the first piezoelectric material in the present embodiment is, as described above, from 0.5 up to but not including 1.0, preferably from 0.7 up to but not including 1.0, and more preferably from 0.8 up to but not including 1.0.

Adopting a degree of orientation F of the first piezoelectric material of 0.5 or more results in a large number of molecular chains of the helical chiral polymer (A) (for example, the molecular chains of polylactic acid) being arranged in the stretching direction. This results in a high ratio of oriented crystals being generated, and enables higher piezoelectric properties to be exhibited.

Longitudinal cleavage strength is further improved when the degree of orientation F of the first piezoelectric material is less than 1.0.

(Degree of Crystallinity)

The degree of the crystallinity of the first piezoelectric material in the present embodiment is a value measured by the above X-ray diffraction measurement (wide-angle x-ray diffraction measurement).

The degree of crystallinity of the first piezoelectric material in the present embodiment is preferably from 20% to 80%, more preferably from 25% to 70%, and still more preferably from 30% to 60%.

High piezoelectric properties are maintained by adopting a degree of crystallinity of 20% or more. A high transparency is maintained in the first piezoelectric material by adopting a degree of crystallinity of 80% or less.

Adopting a degree of crystallinity of 80% or less facilitates production of the first piezoelectric material, due to whitening or breaking being less likely to occur when, for example, the first piezoelectric material is being produced by stretching a piezoelectric film that serves as raw material therefor. Adopting a degree of crystallinity of 80% or less results in a fiber with high flexibility and suppleness characteristics in cases in which, for example, production is performed by stretching a raw material for the first piezoelectric material (for example, polylactic acid) after melt spinning, thereby enabling the first piezoelectric material to be easily produced.

(Transparency (Internal Haze))

Transparency is not particularly required for the first piezoelectric material in the present embodiment, but the first piezoelectric material may, of course, have transparency.

The transparency of the first piezoelectric material can be evaluated by measuring an internal haze. The internal haze of the first piezoelectric material referred to here refers to a haze obtained by excluding haze caused by the profile of the outer surface of the first piezoelectric material.

When there are requirements for transparency, the internal haze for visible light of the first piezoelectric material is preferably 5% or less, and, from the viewpoint of further improving transparency and longitudinal cleavage strength, is more preferably 2.0% or less, and is still more preferably 1.0% or less. There is no particular lower limit value for the internal haze of the first piezoelectric material and the lower limit value may, for example, be set at 0.01%.

The internal haze of the first piezoelectric material is a value measured for a first piezoelectric material having a thickness of from 0.03 mm to 0.05 mm at 25° C. in accordance with JIS-K7105 by using a haze measuring machine (TC-HIII DPK, manufactured by Tokyo Denshoku Co., Ltd.).

An example of a method of measuring the internal haze of the first piezoelectric material will be described below.

First, a sample 1 consisting of a silicone oil (SHIN-ETSU SILICONE (trademark), product number: KF96-100CS, manufactured by Shin-Etsu Chemical Co., Ltd.) alone sandwiched between two glass sheets is prepared, and the haze (hereinafter referred to as "haze (H2)") of the sample 1 is measured in the thickness direction.

Then, a sample 2 is prepared by arranging plural strands of the first piezoelectric material uniformly coated on the surface with a silicone oil next to each other without any gaps therebetween, sandwiched between two glass sheets, and the haze (hereinafter referred to as "haze (H3)") of the sample 2 is measured in the thickness direction.

The internal haze (H1) of the first piezoelectric material is then obtained by finding the difference between the hazes as described in the following Formula.

Internal haze (H1)=haze (H3)−haze (H2)

The haze (H2) and the haze (H3) are each measured here using the following apparatus under the following measurement conditions.
Measurement apparatus: HAZE METER TC-HIIIDPK, manufactured by Tokyo Denshoku Co., Ltd.
Sample size: 30 mm in width×30 mm in length
Measurement conditions: based on JIS-K7105
Measurement temperature: room temperature (25° C.)
(Shape and Dimensions of First Piezoelectric Material)

The piezoelectric substrate of the present embodiment includes the elongate first piezoelectric material.

The elongate first piezoelectric material is preferably a piezoelectric material having a fiber shape (yarn-form) configured from a single or plural bundles, or a piezoelectric material having an elongate flat plate shape.

The piezoelectric material having a fiber shape (hereinafter also referred to as "fibrous piezoelectric material") and the piezoelectric material having an elongate flat plate shape (hereinafter also referred to as "elongate-flat-plate-shaped piezoelectric material") will be described in sequence below.
—Fibrous Piezoelectric Material—

Examples of the fibrous piezoelectric material include monofilament yarn and multifilament yarn.
Monofilament Yarn The monofilament yarn preferably has a single yarn fineness of from 3 dtex to 30 dtex, and more preferably from 5 dtex to 20 dtex.

Handling the yarn is difficult in textile preparation processes and weaving processes when the single yarn fineness is less than 3 dtex. However, fusion between yarns readily occurs when the single yarn fineness is more than 30 dtex.

Cost considerations mean that monofilament yarn is preferably obtained by direct spinning and stretching. The monofilament yarn may be a procured yarn.
Multifilament Yarn The overall fineness of multifilament yarn is preferably from 30 dtex to 600 dtex, and more preferably from 100 dtex to 400 dtex.

For example, both one-step yarns such as a spin-draw yarn, and also two-step yarns obtained by stretching such as those UDY (undrawn yarn), POY (high orientation undrawn yarn), or the like, are employable as the multifilament yarn. The multifilament yarn may be a procured yarn.

ECODEAR® PLA manufactured by Toray Industries, Inc., TERRAMAC® manufactured by Unitika Ltd., and PLASTARCH® manufactured by KURARAY CO., LTD. are employable as commercially available products of polylactic acid-based monofilament yarn and polylactic acid-based multifilament yarn.

The method of producing the fibrous piezoelectric material is not particularly limited, and any known method may be employed for production.

For example, a filament yarn (monofilament yarn or multifilament yarn) may be obtained as the first piezoelectric material by melt-spinning raw material (for example, polylactic acid) and then stretching the material (i.e. a melt-spinning stretching method). After spinning, the ambient temperature of the vicinity of the yarn is preferably maintained in a certain temperature range until cooling and solidification has occurred.

A filament yarn may be obtained as the first piezoelectric material by, for example, further separating fibers from a filament yarn obtained by the melt-spinning stretching method described above.
Cross-Sectional Profile Various cross-sectional profiles may be employed as the cross-sectional profile of the fibrous piezoelectric material, such as a circular profile, an elliptical profile, a rectangular profile, a cocoon profile, a ribbon profile, a four-leafed profile, a star profile, and an irregular profile for cross-sections perpendicular to the longitudinal direction of the fibrous piezoelectric material.
—Elongate-Flat-Plate-Shaped Piezoelectric Material—

Examples of the elongate-flat-plate-shaped piezoelectric material include an elongate-flat-plate-shaped piezoelectric material (for example, a slit ribbon) obtained by slitting a piezoelectric film produced by a known method or a procured piezoelectric film.

Use of the elongate-flat-plate-shaped piezoelectric material as the first piezoelectric material enables close face-contact to be achieved with the conductor, thereby enabling charge generated by a piezoelectric effect to be efficiently detected as a voltage signal.

The elongate-flat-plate-shaped piezoelectric material (first piezoelectric material) in the present embodiment preferably includes a functional layer arranged on at least one principal face of the first piezoelectric material.

The functional layer may have a single-layer structure or may be a structure configured from two or more layers.

For example, in cases in which there are functional layers arranged on both principal faces of the elongate-flat-plate-shaped piezoelectric material, a functional layer arranged on the principal face on one side (hereinafter referred to as the "front face" for convenience) and a functional layer arranged on the face on the other side (hereinafter referred to as "back face" for convenience) may, independently, each have a single-layer structure or a structure configured from two or more layers.

There are various examples of functional layers that may be employed as the functional layer.

Examples of the functional layer include an adhesion-facilitation layer, a hard coat layer, a refractive index adjustment layer, an antireflection layer, an antiglare layer, a sliding-facilitation layer, an anti-blocking layer, a protective layer, an adhesive layer, an antistatic layer, a heat dissipation layer, an ultraviolet absorbing layer, an anti-Newton ring layer, a light scattering layer, a polarizing layer, a gas barrier layer, a hue adjustment layer, and an electrode layer.

The functional layer may be a layer including two or more layers from out of such layers.

The functional layer may be a layer having two or more of such functions.

In cases in which the functional layers are disposed on both principal faces of the elongate-flat-plate-shaped piezoelectric material, the functional layer arranged on the front face side and the functional layer arranged on the back face side may be the same type of functional layer or different types of functional layer.

Examples of the effects of the functional layer include the effect of filling defects such as die lines and dents in the surface of the elongate-flat-plate-shaped piezoelectric material so as to improve the appearance thereof. In such cases, the smaller the difference between the refractive indices of the elongate-flat-plate-shaped piezoelectric material and the functional layer, the more that reflection is reduced at the interface between the elongate-flat-plate-shaped piezoelectric material and the functional layer, and the greater the improvement in appearance.

The functional layer preferably includes at least one of an adhesion-facilitation layer, a hard coat layer, an antistatic layer, an anti-blocking layer, a protective layer, or an electrode layer. Adopting such an approach further facilitates application to, for example, a piezoelectric device (such as a piezoelectric textile or a piezoelectric fabric), a force sensor, an actuator, or a biodata acquisition device.

The functional layer more preferably includes an electrode layer.

The electrode layer may be provided so as to be in contact with the elongate-flat-plate-shaped piezoelectric material, or may be disposed with a functional layer other than the electrode layer interposed therebetween.

A particularly preferred aspect of the elongate-flat-plate-shaped piezoelectric material (first piezoelectric material) in the present embodiment is an aspect including functional layers provided on both principal faces of the elongate-flat-plate-shaped piezoelectric material, with both of the functional layers including an electrode layer.

In the elongate-flat-plate-shaped piezoelectric material (first piezoelectric material) in the present embodiment, at least one surface layer of a layered body including the first piezoelectric material and the functional layer is preferably an electrode layer. In other words, in the elongate-flat-plate-shaped piezoelectric material (first piezoelectric material) in the present embodiment, preferably at least one out of the surface layer on the front face side or the surface layer of the back face side is an electrode layer (i.e., the electrode layer is preferably exposed).

This thereby enables the conductor (preferably an inner conductor) or the first outer conductor to be more easily connected to the layered body in cases in which the elongate-flat-plate-shaped piezoelectric material is used as one of the configuration elements of, for example, a piezoelectric device (such as a piezoelectric textile or a piezoelectric fabric), a force sensor, an actuator, or a biodata acquisition device. This raises the ease of manufacturing the piezoelectric device (such as a piezoelectric textile or a piezoelectric fabric), the force sensor, the actuator, or the biodata acquisition device.

There is no particular limitation to the material of the functional layer, and examples thereof include: an inorganic substance such as a metal or a metal oxide; an organic substance such as a resin; a composite composition including a resin and fine particles; and the like. Examples of substances that may be employed as such a resin include a cured resin obtained by curing using heat or actinic-radiation energy. In other words, a curable resin may be used as the resin.

Examples of the curable resin include at least one material (curable resin) selected from the group consisting of an acrylic-based compound, a methacrylic-based compound, a vinyl-based compound, an allyl-based compound, a urethane-based compound, an epoxy-based compound, an epoxide-based compound, a glycidyl-based compound, an oxetane-based compound, a melamine-based compound, a cellulose-based compound, an ester-based compound, a silane-based compound, a silicone-based compound, a siloxane-based compound, a silica-acryl hybrid compound, and a silica-epoxy hybrid compound.

Among these, an acrylic-based compound, an epoxy-based compound, and a silane-based compound are more preferred.

Examples of the metal include at least one selected from Al, Si, Ti, V, Cr, Fe, Co, Ni, Cu, Zn, In, Sn, W, Ag, Au, Pd, Pt, Sb, Ta, or Zr, or an alloy thereof.

Examples of the metal oxide include titanium oxide, zirconium oxide, zinc oxide, niobium oxide, antimony oxide, tin oxide, indium oxide, cerium oxide, aluminum oxide, silicon oxide, magnesium oxide, yttrium oxide, ytterbium oxide, tantalum oxide, and at least one composite oxide thereof.

Examples of the fine particles include: fine particles of metal oxides such as those described above; resin fine particles such as fine particles of a fluorine-based resin, a silicone-based resin, a styrenic-based resin, an acrylic-based resin, and the like. Examples also include hollow fine particles configured with internal pores in such fine particles.

From the viewpoint of transparency, the average primary particle diameter of the fine particles is preferably from 1 nm to 500 nm, more preferably from 5 nm to 300 nm, and still more preferably from 10 nm to 200 nm. An average primary particle diameter of 500 nm or less results in suppression of visible light scattering, while an average primary particle diameter of 1 nm or more results in suppression of the secondary aggregation of the fine particles, this being desirable to achieve from the viewpoint of maintaining transparency.

The film thickness of the functional layer is not particularly limited, and is preferably in a range of from 0.01 μm to 10 μm.

The above upper limit value to the thickness is more preferably 6 μm or less, and still more preferably 3 μm or less. The lower limit value thereof is more preferably 0.01 μm or more, and still more preferably 0.02 μm or more.

The above thickness represents the thickness of the entire multilayer film in cases in which the functional layer is a multilayer film configured from plural functional layers. There may be a functional layer on each face of the elongate-flat-plate-shaped piezoelectric material. The refractive indices of the functional layers may be values different from each other.

There are no particular limitations to the method of producing the elongate-flat-plate-shaped piezoelectric material, and the elongate-flat-plate-shaped piezoelectric material may be produced by a known method.

For example, a method to produce a first piezoelectric material from a piezoelectric film is to mold raw material (for example, polylactic acid) into a film-form to obtain an unstretched film, to stretch and crystallize the obtained unstretched film, and then to slit the obtained piezoelectric film.

"Slitting" here means cutting the piezoelectric film is cut into an elongated shape.

Either the stretching or the crystallization may be performed first. A method may also be adopted in which the unstretched film is sequentially subjected to preliminary crystallization, then stretching, and then crystallization (annealing). Such stretching may be monoaxial stretching or biaxial stretching. In cases in which biaxial stretching is performed, a higher stretching ratio is preferably set in one direction (the principal stretching direction).

The method for producing the piezoelectric film may be performed with appropriate reference to known literature such as Japanese Patent No. 4934235, WO 2010/104196, WO 2013/054918, and WO 2013/089148.

<Second Piezoelectric Material>

The piezoelectric substrate of the first embodiment may include an elongate second piezoelectric material.

The second piezoelectric material preferably has characteristics similar to those of the first piezoelectric material.

In other words, the second piezoelectric material preferably includes an optically active helical chiral polymer (A), a lengthwise direction of the second piezoelectric material and a principal orientation direction of the helical chiral polymer (A) included in the second piezoelectric material are substantially parallel to each other, and a degree of orientation F of the second piezoelectric material, determined from X-ray diffraction measurement by the above Formula (a), is in a range of from 0.5 up to but not including 1.0.

The second piezoelectric material also preferably has characteristics similar to those of the first piezoelectric material for characteristics other than the above.

However, the winding directions of the first piezoelectric material and the second piezoelectric material, and the chiralities of the helical chiral polymers (A) included in the first piezoelectric material and the second piezoelectric material may be appropriately selected according to the aspect of the piezoelectric substrate from the viewpoint of better exhibiting the effects of the present embodiment.

Examples of preferred combinations of the winding directions of the first piezoelectric material and the second piezoelectric material and the chiralities of the helical chiral polymers (A) included in the first piezoelectric material and the second piezoelectric material are as described above in the specific aspects.

The second piezoelectric material may have characteristics different from those of the first piezoelectric material.

<First Insulator>

The piezoelectric substrate of the first embodiment may further include a first insulator.

The first insulator is preferably helically wound around the outer peripheral surface of the inner conductor.

In such cases, the first insulator may be arranged at the opposite side from the inner conductor as viewed from the first piezoelectric material, or may be interposed between the inner conductor and the first piezoelectric material.

The winding direction of the first insulator may be the same direction as the winding direction of the first piezoelectric material or a different direction therefrom.

This is advantages particularly in cases in which the piezoelectric substrate of the first embodiment includes a first outer conductor, since further including the first insulator in the piezoelectric substrate according to the first embodiment makes it easier to suppress the occurrence of an electrical short circuit between the inner conductor and the outer conductor when the piezoelectric substrate undergoes bending deformation.

The first insulator is not particularly limited, and examples thereof include a vinyl chloride resin, a polyethylene resin, a polypropylene resin, an ethylene-tetrafluoroethylene copolymer (ETFE), a tetrafluoroethylene-hexafluoropropylene copolymer (FEP), a tetrafluoroethylene resin (PTFE), a tetrafluoroethylene-perfluoropropylvinylether copolymer (PFA), a fluororubber, a polyester resin, a polyimide resin, a polyamide resin, a polyethylene terephthalate resin (PET), and a rubber (including an elastomer).

The shape of the first insulator is preferably an elongate shape from the viewpoint of winding around the conductor.

<Second Insulator>

The piezoelectric substrate of the present embodiment may, in cases in which a first outer conductor is provided at an outer periphery thereof, further include a second insulator provided at the outer periphery of the first outer conductor.

Adopting such an approach enables the inner conductor configuring the signal line to be electrostatically shielded, and suppresses voltage fluctuations in the conductor (preferably an inner conductor) due to the effects of external static electricity.

The second insulator is not particularly limited, and examples thereof include the materials described in the examples of the first insulator.

The shape of the second insulator is not particularly limited, and any shape capable of covering at least a portion of the first outer conductor may be adopted therefor.

(First Outer Conductor)

The piezoelectric substrate of the present embodiment preferably further includes a first outer conductor at an outer periphery.

The first outer conductor in the present embodiment is preferably a ground conductor.

The ground conductor refers to, for example, a conductor paired with the conductor (preferably a signal line conductor) when a signal is being detected.

The material of the ground conductor is not particularly limited, and main examples thereof include the following materials according to the cross-sectional profile thereof.

For example, materials that may be used as the material of a ground conductor having a rectangular cross-section include a copper foil ribbon obtained by rolling a copper wire of a circular cross-section so as to process the copper wire into a flat plate shape, an Al foil ribbon, and the like.

For example, materials that may be used as the material of a ground conductor having a circular cross-section include a copper wire, an aluminum wire, an SUS wire, a metal wire covered with an insulating layer, a carbon fiber, a resin fiber integrated together with a carbon fiber, and a tinsel wire obtained by spirally winding a copper foil around a fiber.

A material obtained by coating an organic conductive material with an insulating material may be used as the material of the ground conductor.

The ground conductor is preferably arranged to wrap around the conductor (preferably a signal line conductor) and the first piezoelectric material so as to avoid short circuiting with the signal line conductor.

A method of wrapping such a signal line conductor may be a wrapping method selected from a method of helically winding a copper foil or the like, a method of making a copper wire or the like into a cylindrical braid and then wrapping such a signal line conductor therein, or the like.

The method of wrapping the signal line conductor is not limited to these methods. Wrapping the signal line conductor enables electrostatic shielding to be performed, and enables voltage fluctuations in the signal line conductor due to the effects of external static electricity to be prevented.

A preferable aspect is also an arrangement of the ground conductor so as to be arranged by wrapping in a cylindrical shape so as to enclose a minimum basic configuration unit (i.e., the conductor and the first piezoelectric material) of the piezoelectric substrate of the present embodiment.

Various cross-sectional profiles may be employed as the cross-sectional profile of the ground conductor, such as a circular profile, an elliptical profile, a rectangular profile, and an irregular profile. In particular, a rectangular cross-section enables close contact to be achieved by flat-faces with the conductor (preferably a signal line conductor), the first piezoelectric material, and, according to circumstances, with the first insulator, the second piezoelectric material, or the like, thereby enabling charge generated by a piezoelectric effect to be efficiently detected as a voltage signal.

<Adhesive Agent to Form Adhesive Layer>

The piezoelectric substrate of the present embodiment preferably includes an adhesive layer between the conductor and the first piezoelectric material.

The adhesive agent to form the adhesive layer is used in order to mechanically integrate the conductor and the first piezoelectric material together or to maintain an inter-electrode distance (between the conductor and the outer conductor) in cases in which the piezoelectric substrate includes an outer conductor.

Providing the adhesive layer between the conductor and the first piezoelectric material inhibits the relative position of the conductor and the first piezoelectric material from shifting when tension has been applied to the piezoelectric substrate of the present embodiment, thereby facilitating application of tension to the first piezoelectric material. This accordingly enables a voltage output proportional to the tension to be effectively detected from the conductor (preferably a signal line conductor). As a result, piezoelectric sensitivity and piezoelectric output stability are further improved. Providing the adhesive layer results in a further increase in the absolute value of the amount of generated charge per unit tensile force.

However, since suppleness is maintained after processing a piezoelectric substrate lacking an adhesive layer between a conductor and a first piezoelectric material into a piezoelectric fiber, this approach results in a favorable feeling of fit when employed in a wearable sensor or the like.

The following materials may be used as the material of the adhesive agent to form the adhesive layer.

Examples of adhesive agents that may be used therefor include an epoxy-based adhesive agent, a urethane-based adhesive agent, a vinyl acetate resin-based emulsion type adhesive agent, an (EVA)-based emulsion type adhesive agent, an acrylic resin-based emulsion type adhesive agent, a styrene-butadiene rubber-based latex type adhesive agent, a silicone resin-based adhesive agent, an α-olefin (isobutene-maleic anhydride resin)-based adhesive agent, a vinyl chloride resin-based solvent type adhesive agent, a rubber-based adhesive agent, an elastic adhesive agent, a chloroprene rubber-based solvent type adhesive agent, a nitrile rubber-based solvent type adhesive agent or the like, and a cyanoacrylate-based adhesive agent or the like.

—Elastic Modulus—

The adhesive agent in the present embodiment preferably has an elastic modulus after bonding that is either equivalent to, or greater than, that of the first piezoelectric material. If the material used has an elastic modulus lower than the elastic modulus of the first piezoelectric material, then strain (piezoelectric strain) caused by tension that has been applied to the piezoelectric substrate of the present embodiment would be attenuated by the adhesive agent portion, decreasing the transfer efficiency of strain to the first piezoelectric material. This results in the sensitivity of a sensor being prone to decrease in cases in which the piezoelectric substrate of the present embodiment is applied to a sensor, for example.

—Thickness—

The thickness at sites bonded by the adhesive agent in the present embodiment is preferably as thin as possible within a range in which there are no voids between the bonding targets and bonding strength does not decrease. Decreasing the thickness at the bonded sites makes it less likely that strain caused by tension that has been applied to the piezoelectric substrate is attenuated by the adhesive agent portion, and the strain on the first piezoelectric material is efficiently decreased. This results in the sensitivity of a sensor being improved in cases in which the piezoelectric substrate of the present embodiment is applied to a sensor, for example.

—Method of Applying Adhesive Agent—

The method of applying the adhesive agent is not particularly limited, and the following two methods are primarily used therefor.

Method of Interposing Adhesive Agent and Performing Bonding after Processing

Examples thereof include a method in which: a conductor (preferably a signal line conductor) and a first piezoelectric material are arranged; the signal line conductor and a ground conductor are processed and arranged; and then, after this has been completed, an adhesive agent is interposed and adhered at an interface between the conductor and the first piezoelectric material by a method such as dip coating, impregnation, or the like.

In the above method, as well as bonding the conductor and the first piezoelectric material to each other, bonding may also be performed between each member that has, if necessary, been included in the piezoelectric substrate of the present embodiment.

Method of Interposing Uncured Adhesive Agent Before Processing, and Performing Bonding after Processing Examples thereof include a method in which a photo-curable adhesive agent, a thermosetting adhesive agent, a thermoplastic adhesive agent, or the like is coated in advance onto a surface of a first piezoelectric material using a gravure coater, a dip coater, or the like, and then dried. Then after completing arrangement of a conductor and the first piezoelectric material, the adhesive agent is then cured by ultraviolet irradiation or heat so as to bond an interface between the conductor and the first piezoelectric material.

In the above method, as well as bonding the conductor and the first piezoelectric material to each other, bonding may also be performed between each member that has, if necessary, been included in the piezoelectric substrate of the present embodiment.

Using the above method enables processing to be performed by dry processes, after the adhesive agent has been coated and dried, thereby facilitating processing or facilitating formation of a uniform film thickness. This results in characteristically small variations in sensor sensitivity and the like.

<Method of Producing Piezoelectric Substrate>

The method of producing the piezoelectric substrate of the present embodiment is not particularly limited, and the piezoelectric substrate may be produced, for example, by preparing a first piezoelectric material and helically winding the first piezoelectric material around a separately prepared conductor (preferably a signal line conductor) in one direction.

The first piezoelectric material may also be produced by a known method and may also be procured.

In cases in which the piezoelectric substrate of the present embodiment includes, if necessary, a second piezoelectric material and a first insulator, such a piezoelectric substrate may be produced in accordance with the methods for helically winding the first piezoelectric material.

However, the directions of winding the first piezoelectric material and the second piezoelectric material, and the chiralities of the helical chiral polymers (A) included in the first piezoelectric material and the second piezoelectric material, are preferably selected in accordance with the aspects of the piezoelectric substrate described above.

In cases in which the piezoelectric substrate of the present embodiment includes a first outer conductor (for example, a ground conductor), such a piezoelectric substrate may be produced by arranging the first outer conductor using the above methods or a known method.

If necessary, the conductor and the first piezoelectric material, and each member included in the piezoelectric substrate of the present embodiment, may be stuck together by interposing an adhesive agent therebetween using, for example, the method described above.

In the piezoelectric substrate of the present embodiment, due to the application of tensile force, shearing strain proportional to the tensile force is applied to a helical chiral (A) and detected as a voltage signal (charge signal) from the conductor.

Operation

The bed device 10 of the present embodiment operates in the following manner.

As illustrated in FIG. 2, the sensor unit 32 is installed on the bed boards 24 in the present embodiment such that the array direction of the regions 34 is oriented in a predetermined direction of the bed width direction. Accordingly, when a person in bed is present in a recumbent position on the mattress 26, pressure is applied in the sensor unit 32 by the body of the person in bed in radial directions of the piezoelectric substrates 12 in each of the regions 34. As a result, a voltage corresponding to the pressure is output for each of the piezoelectric substrates 12. The voltages output from each of the piezoelectric substrates 12 are input to the AD converter 42, and the output voltages of the analog signals are converted into digital signals and output to the processing PC 50. The detection section 55 detects the digital signals so as to enable the processing PC 50 to detect whether or not there is a person in bed present on the mattress 26, and also on which of the detection regions 27 (regions 34) they are sleeping. For example, cases in which the voltage output V of one of the piezoelectric substrates 12 has exceeded a threshold value Vt enable the person in bed to be detected as sleeping in the region 34 corresponding to that piezoelectric substrate 12, namely in the corresponding detection region 27 on the mattress 26.

Since the processing PC 50 of the human body detection device 30 is provided with the determination section 56, the bed device 10 of the present embodiment is also capable of configuring a human body detection system capable of detecting when the person in bed has turned over in bed. In the bed device 10 configuring such a human body detection system, the regions 34 are provided along a predetermined direction of the bed width direction in the reference plane 33, and the respective piezoelectric substrates 12 are arranged in each of the regions 34. The determination section 56 is capable of determining movement of the person in bed on the mattress 26 (or the reference plane 33) by comparing the voltages output from piezoelectric substrates 12 adjacent to each other in the bed width direction. The actual moments when the voltage outputs V of respective piezoelectric substrates 12 exceeded the threshold value Vt are recorded by the detection section 55 of the processing PC 50, enabling the fact that the person in bed has turned over in bed and the direction in which they turned over to be determined by the determination section 56 from the sequence in which the piezoelectric substrates 12 exceeded the threshold value Vt.

The present embodiment enables not only obviously the presence or absence of a sleeping person to be detected, but also enables the position on the bed surface of the bed 20 to be detected. Using the processing PC 50 enables monitoring of whether the person in bed is at a lopsided position on the bed surface, and enables the person in bed and a carer to be notified. This enables falls from the bed 20 and the like to be averted.

The sensor unit 32 of the present embodiment is provided with the line shaped piezoelectric substrates 12. There is therefore no constraint to the arrangement thereof within the regions 34. For example, a wavy arrangement or a whorled arrangement along the reference plane 33 in the regions 34 enables variations to be made to the directionality and sensitivity of pressure detection. Moreover, although the bed width direction is partitioned into four of the regions 34 in the present embodiment, there is no limitation thereto, and more than four partitions may be provided, or partitions may be added in the bed lengthwise direction. This enables an increase to be achieved in the resolution with which the body of the person in bed is detected.

Moreover, the piezoelectric substrate 12 includes the elongate first piezoelectric material 18A helically wound in one direction around the inner conductor 16A, and a feature thereof is that the pressure input to the first piezoelectric material 18A is detected from the potential difference between the inner conductor 16A and the first piezoelectric material 18A. In the bed device 10 of the present embodiment, employing piezoelectric material as a sensor to detect pressure obviates the need for a power source to supply the sensor. Power is accordingly not consumed when in a standby state, in contrast to use of a sensor to detect pressure configured by a strain gauge or load cell, for example. Namely, being able to drive using a simple circuit lends itself to a reduction in size. Moreover, since the polylactic acid employed in the piezoelectric material is cheaper than a load cell the manufacturing costs incurred for the sensor sections is also suppressed.

Notes

The human body detection device 30 of the present embodiment may be configured as a bed device 10 incorporated into an existing bed 20, or may be employed by installing in a rug, flooring, tatami mat, or the like. The human body detection device 30 exhibits the similar operation and advantageous effects to those of the bed device 10 described above when installed in a rug, flooring, tatami mat, or the like. Being able to combine the human body detection device 30 of the present embodiment with existing bedding enables use with bedding already to hand, enabling any detriment to sleep comfort to be suppressed.

Although the piezoelectric substrates 12 are covered by the insulating members 38 in the bed device 10 of the present embodiment, there is no limitation thereto, and the piezoelectric substrates 12 may be arranged directly between the mattress 26 and the shock absorbing material 37. Tension is imparted to the piezoelectric substrate 12 by strain induced by compressional load on the shock absorbing material 37 from a human body or the like on the bed 20. This enables the sensitivity of the piezoelectric substrate 12 to be raised when the shock absorbing material 37 undergoes a large strain for a given load. Namely, materials that are soft and have a low elastic modulus, a low rubber hardness, and a low density are well suited to being employed for the shock absorbing material 37 in order to achieve a high sensing sensitivity with the piezoelectric substrate 12. Specific examples of such materials include suitable foamed resin materials of low elastic modulus. Examples of materials employed as such foamed resin materials include soft polyurethane foams, hard polyurethane foams, polystyrene foams, polyethylene foams, polypropylene foams, EVA crosslinked foams, PET resin foams, phenol foams, silicone foams, polyvinyl chloride foams, urea foams, acrylic foams, polyimide foams, EPDM foams, and the like. However, if the elastic modulus, rubber hardness, and density of the material configuring the shock absorbing material 37 is too low, then the pores of the shock absorbing material 37 collapse under the strain induced by a large compressional load, and strain becomes difficult to induce, making high sensing sensitivity difficult to achieve. The thickness of the shock absorbing material 37 is accordingly optimized as appropriate for the load imparted so as not to fall into a compressional deformation range in which strain is difficult to induce.

Moreover, with foamed plastics, the variation in the density and rubber hardness is higher as the expansion ratio increases, resulting in a greater variation in the sensing sensitivity of the piezoelectric substrate 12. Materials such as natural rubber and the like also suffer from large changes in rubber hardness over time, resulting in large variations in sensing sensitivity. EPDM foams and the like that only undergo small changes over time are accordingly well suited therefor. Moreover, flame resistance is often demanded when the shock absorbing material 37 is employed in the bed 20. Foamed plastics having a type of flame resistant additive blended therein to induce flame resistance are accordingly suitably employed for the material of the shock absorbing material 37 in such cases, or alternatively polyvinyl chloride foams, polyimide foams, or the like that have flame resistance in the resin itself are also suitably employed therefor.

Alternatively, the piezoelectric substrates 12 may be arranged directly between the mattress 26 and the support plate 36 without providing the shock absorbing material 37.

Moreover, the support plate 36 is not essential in the bed devices of each embodiment, and the shock absorbing material 37 may be provided on the bed boards 24. In such cases, the piezoelectric substrates 12 may be arranged directly between the mattress 26 and the shock absorbing material 37, or may be arranged directly between the mattress 26 and the bed boards 24.

Although the insulating member 38 serving as a covering member in the present embodiment is configured by an adhesive tape or an adhesive film, there is no limitation thereto. Examples of forms of the insulating member 38 include laminates, heat shrink tubes, or coverings of insulating materials (for example, a PET or fluoro-tape wound around a piezoelectric line).

The processing for the detection section 55, the determination section 56, and the notification section 57 achieved by the CPU 50A reading and executing software (programs) in the present embodiment may be executed by various processors other than a CPU. Examples of such processors include programmable logic devices (PLD) with circuit configurations that can be modified post-manufacture, such as a field-programmable gate array (FPGA), or dedicated electrical circuits configuring a processor with dedicated designed circuit configurations for executing specific processing, such as an application specific integrated circuits (ASIC). Moreover, the various processing may be executed by a single processor of such type, or by a combination of two or more processors of the same or different types (for example by plural FPGAs, or a combination of a CPU and an FPGA). Hardware structures of such processors are more specifically electrical circuits combining circuit elements such as semiconductor elements.

Although a format in which the execution program is stored (installed) in advance in the storage 50D is adopted in the above embodiment, there is no limitation thereto. The program may be provided recorded on a recording medium such as compact disc read only memory (CD-ROM), digital versatile disc read only memory (DVD-ROM), or universal serial bus (USB) memory. Moreover, the program may be in a format to be downloaded from an external device over a network.

Second Embodiment

Figure 9:
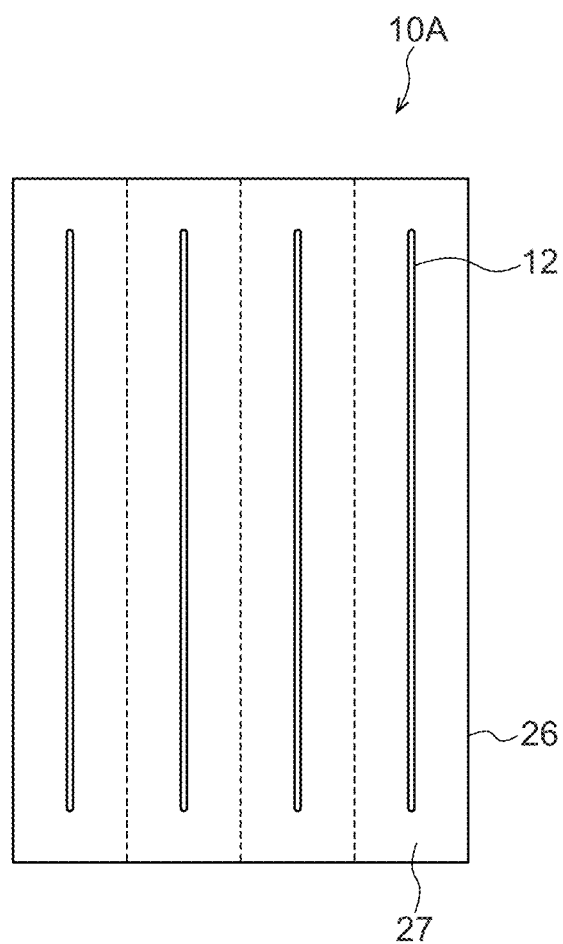
FIG. 9 is a plan view illustrating an arrangement of piezoelectric substrates on a bed device according to a second embodiment.

Explanation follows regarding a bed device 10A of a second embodiment, with reference to FIG. 9.

The bed device 10A of the second embodiment differs from the first embodiment in the arrangement of the piezoelectric substrates 12. Note that FIG. 9 only illustrates the arrangement of the piezoelectric substrates 12 to the mattress 26, and the frame 22, the bed boards 24, the support plate 36, the shock absorbing material 37, and the insulating member 38 are omitted from illustration (the same applies to FIG. 10 to FIG. 12 below). Explanation follows regarding the points of difference from the first embodiment.

In the mattress 26 of the present embodiment the bed width direction is partitioned into four detection regions 27, similarly to in the first embodiment. However, the piezoelectric substrates 12 in each of the detection regions 27 are arranged along the bed lengthwise direction.

In cases in which the piezoelectric substrates 12 are arranged along the bed width direction as in the first embodiment, variation in the precision of detecting pressure does not readily occur in the bed width direction in each of the detection regions 27. However, in contrast thereto, in cases in which the piezoelectric substrates 12 are arranged along the bed lengthwise direction as in the second embodiment, the pressure detection range in the detection regions 27 can be secured along the bed lengthwise direction. Accordingly, variation in the precision of detecting pressure does not readily occur in the bed length direction even in cases in which there is a difference in height between persons in bed who are sleeping on the mattress 26.

Otherwise, the present embodiment exhibits similar operation and advantageous effects to those of the first embodiment described above.

Third Embodiment

Figure 10:
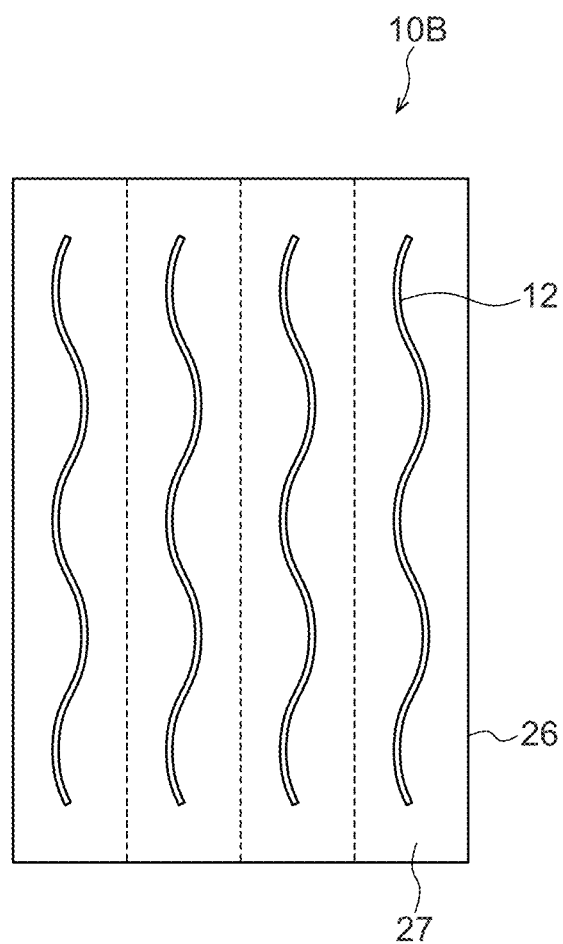
FIG. 10 is a plan view illustrating an arrangement of piezoelectric substrates on a bed device according to a third embodiment.

Explanation follows regarding a bed device 10B of a third embodiment, with reference to FIG. 10.

In the bed device 10B of the third embodiment, the arrangement of the piezoelectric substrates 12 differs from that in the first and second embodiments. Explanation follows regarding the points of difference from the first and second embodiments.

The mattress 26 of the present embodiment is partitioned in the bed width direction into four detection regions 27, similarly to in the first embodiment. However, the piezoelectric substrates 12 are arranged so as to extend in a wavy pattern along the bed lengthwise direction, in each of the detection regions 27, with an amplitude in the bed width direction.

In the bed device 10B of the present embodiment, the pressure detection range in each of the detection regions 27 is configured by a broad range in both the bed lengthwise direction and the bed width direction. Accordingly, in the present embodiment, variation in the precision of detecting pressure does not readily occur in either the bed lengthwise direction or the bed width direction in each of the detection regions 27.

Otherwise, the present embodiment exhibits similar operation and advantageous effects to those of the first embodiment described above.

Fourth Embodiment

Figure 11:
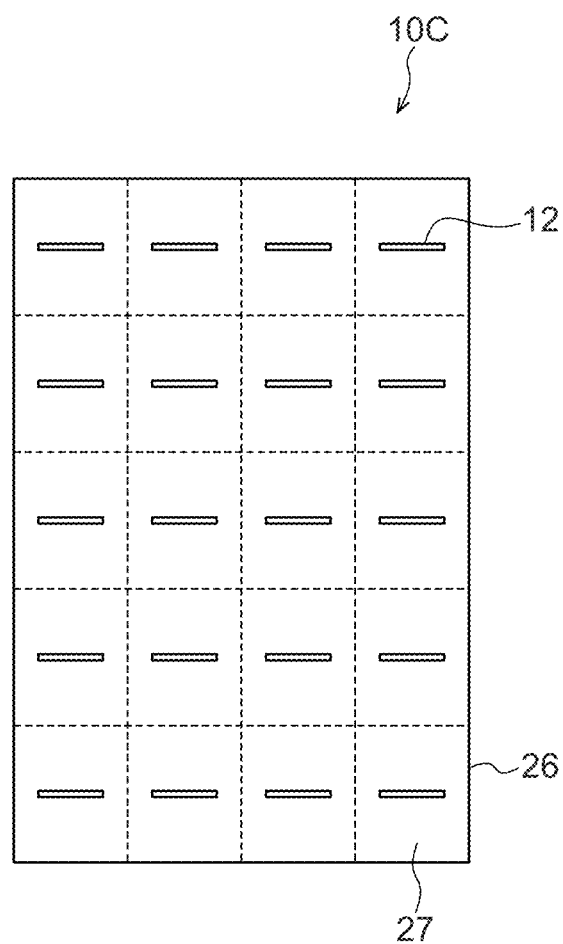
FIG. 11 is a plan view illustrating an arrangement of piezoelectric substrates on a bed device according to a fourth embodiment.

Explanation follows regarding a bed device 10C of a fourth embodiment, with reference to FIG. 11.

In the bed device 10C of the fourth embodiment, the number of partitions of the detection regions 27 in the mattress 26 differs from that in the first embodiment. Explanation follows regarding the points of difference from the first embodiment.

The mattress 26 of the present embodiment is partitioned in the bed width direction into four detection regions 27 configuring a pressure measurement range, and in the bed lengthwise direction into five detection regions 27, to give a total of 20 partitions. A piezoelectric substrate 12 is arranged along the bed width direction in each of the detection regions 27.

In the bed device 10C of the present embodiment, since plural of the piezoelectric substrates 12 are also arranged in the bed lengthwise direction, the pressure detection range can be increased. Moreover, in the present embodiment, the number of the piezoelectric substrates 12 per unit area is increased, enabling the resolution with which the body of the person in bed is detected to be raised.

Note that the arrangement of the piezoelectric substrates 12 as in the present embodiment may be achieved by arranging the sensor units 32 of the first embodiment alongside each other in the bed lengthwise direction, and 20 of the piezoelectric substrates 12 may be arranged on a support plate 36 having a size of the same order as that of the mattress 26.

Otherwise, the present embodiment exhibits similar operation and advantageous effects to those of the first embodiment described above.

Fifth Embodiment

Figure 12:
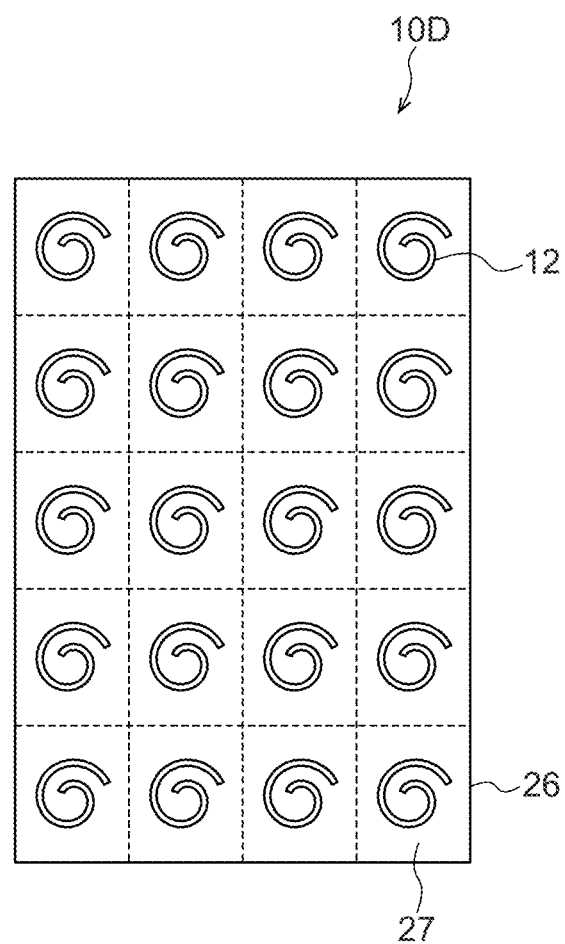
FIG. 12 is a plan view illustrating an arrangement of piezoelectric substrates on a bed device according to a fifth embodiment.

Explanation follows regarding a bed device 10D of a fifth embodiment, reference FIG. 12.

The bed device 10D of the fifth embodiment differs from the fourth embodiment in the arrangement of the piezoelectric substrates 12. Explanation follows regarding points of difference from the first and fourth embodiments.

Similarly to in the fourth embodiment, the mattress 26 of the present embodiment is partitioned into four in the bed width direction and into five in the bed lengthwise direction to give a total of 20 partitions. However, the piezoelectric substrates 12 have a whorled arrangement in each of the detection regions 27.

In the bed device 10D of the present embodiment, similarly to in the fourth embodiment the resolution with which the body of the person in bed is detected can be raised. Moreover, in the present embodiment, the piezoelectric substrates 12 are disposed over a wider range in each of the detection regions 27, such that variation in the precision of detecting pressure in both the bed lengthwise direction and the bed width direction does not readily occur.

Otherwise, the present embodiment exhibits similar operation and advantageous effects to those of the first embodiment described above.

Sixth Embodiment

Figure 15A:
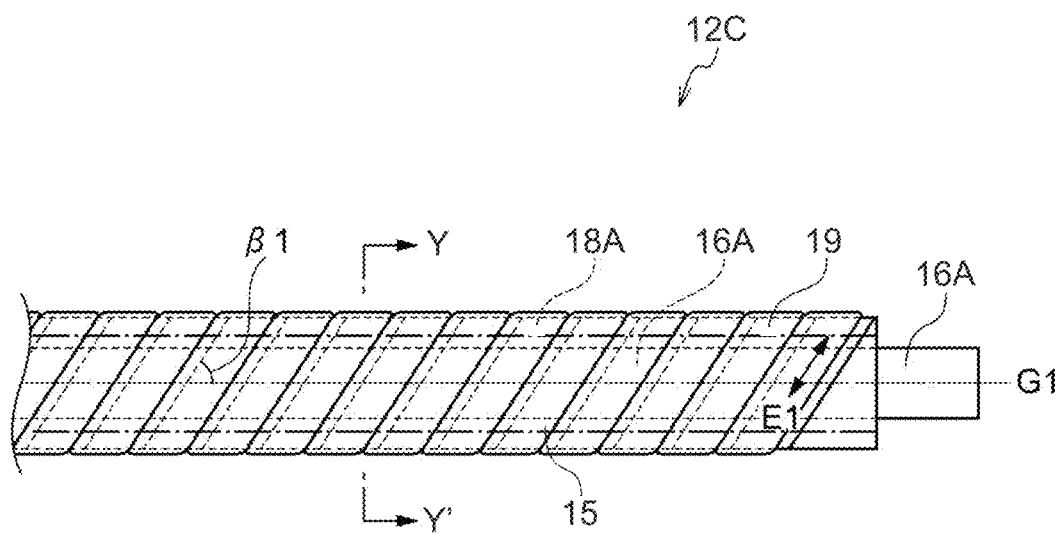
FIG. 15A is a side view illustrating a piezoelectric substrate according to a sixth exemplary embodiment.
Figure 15B:
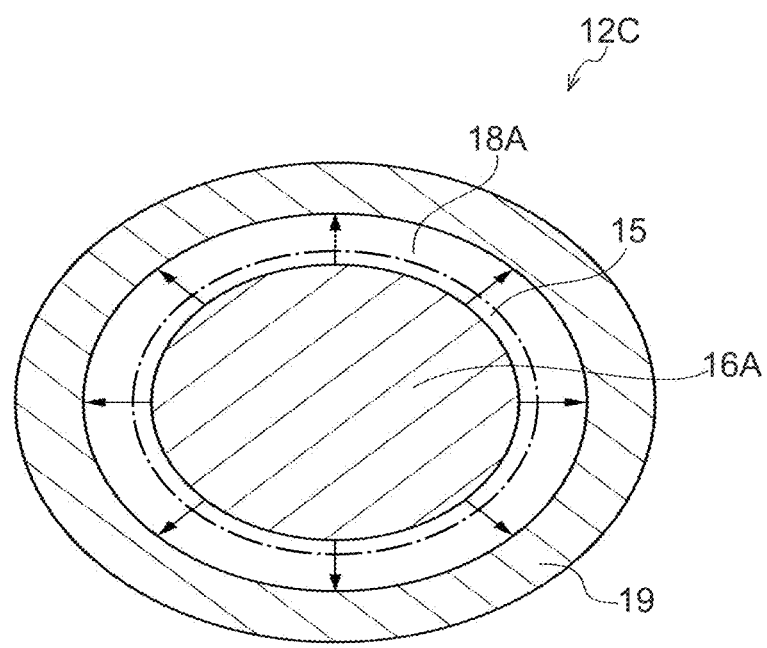
FIG. 15B is a cross-section illustrating a piezoelectric substrate according to the sixth exemplary embodiment (taken along the line Y-Y' of FIG. 15A).

Explanation follows regarding a bed device 10 of a sixth embodiment, with reference to FIG. 15A and FIG. 15B.

The bed device 10 of the sixth embodiment has a similar configuration to that of the bed device 10 of the first embodiment. However, piezoelectric substrates 12C are employed instead of the piezoelectric substrates 12. Explanation follows regarding the points of difference from the first embodiment.

FIG. 15A is a side view illustrating an example of a piezoelectric substrate according to the sixth embodiment.

As illustrated in FIG. 15A, in each of the piezoelectric substrates 12C of the sixth embodiment, an outer conductor 19 is arranged helically wound in one direction around an outer peripheral side thereof. Namely, each of the piezoelectric substrates 12C includes an elongate inner conductor 16A, a functional layer 15, an elongate first piezoelectric material 18A, and an outer conductor 19, in this sequence from inside to outside.

The functional layer 15 is provided on an outer peripheral surface of the inner conductor 16A, and is positioned between the inner conductor 16A and the first piezoelectric material 18A. The functional layer 15 is a layer that is provided as required.

The operation and advantageous effects of the piezoelectric substrate 12C of the sixth embodiment will be described below.

FIG. 15B illustrates a cross-section taken along the line Y-Y' of FIG. 15A. For example, when tension is applied to the piezoelectric substrate 12C in the lengthwise direction thereof, a shear force is applied to the helical chiral polymer (A) included in the first piezoelectric material 18A, thereby polarizing the helical chiral polymer (A). The polarization of the helical chiral polymer (A) is thought to occur along the radial directions of the piezoelectric substrate 12C, as indicated by the arrows in FIG. 15B, with the polarization direction thereof occurring in-phase with each other. As a result, a voltage signal proportional to the tension is detected efficiently.

In particular, in the piezoelectric substrate 12C according to the sixth embodiment, the first piezoelectric material 18A is helically wound in one direction around the outer peripheral surface of the inner conductor 16A without any gaps, such that the inner conductor 16A is not visible. Accordingly, the closeness of contact between the inner conductor 16A and the first piezoelectric material 18A is increased, such that gaps do not readily form between the inner conductor 16A and the outer conductor 19.

As illustrated in FIG. 15B, the piezoelectric substrate 12C according to the sixth embodiment is formed with a non-circular profile, i.e. an elliptical profile, in cross-section perpendicular to its axial center. Due to having this elliptical profile in cross-section perpendicular to its axial center, tightening of resin is suppressed even when tension is applied in a high temperature environment above the glass transition temperature of resin contained in a piezoelectric member, thereby helping to suppress a drop in piezoelectric sensitivity. As illustrated in FIG. 15B, the piezoelectric substrate 12C has an elliptical profile in cross-section perpendicular to its axial center.

This elliptical profile is formed with a dimensional ratio (major axis/minor axis) in a range of, for example, from 1.05 to 10.00. Moreover, the elliptical profile is formed with a flattening ratio in a range of from 0.04 to 0.9.

In the present embodiment, the cross-section of the piezoelectric substrate 12C perpendicular to its axial center is not limited to being an elliptical profile in cross-section. Any non-circular profile may be adopted therefor.

The piezoelectric substrate 12C according to the sixth embodiment is not limited to the above structure. For example, in the piezoelectric substrate 12C an adhesive layer may be arranged as a non-illustrated functional layer between the inner conductor 16A and the first piezoelectric material 18A. So doing makes positional slippage between the first piezoelectric material 18A and the inner conductor 16A less likely to occur, even when tension is applied along the lengthwise direction of the piezoelectric substrate 12C, thereby facilitating the application of tension to the first piezoelectric material 18A.

In the piezoelectric substrate 12C according to the sixth embodiment, as described above, the functional layer 15 is provided between the inner conductor 16A and the first piezoelectric material 18A. The functional layer 15 may also be provided at another appropriate location.

In the piezoelectric substrate 12C according to the sixth embodiment, the outer conductor 19 is arranged so as to be helically wound in one direction around the outer peripheral surface of the piezoelectric substrate 12C. The arrangement of the outer conductor 19 is not limited thereto, and it is sufficient for the outer conductor 19 to be arranged on at least part of the outer periphery of the first piezoelectric material 18A. Moreover, there is no particular limitation to the winding direction of the outer conductor 19.

Hitherto piezoelectric substrates have been employed as piezoelectric members containing resin (polylactic acid etc.). Piezoelectric sensitivity drops when piezoelectric substrates are in a high temperature environment exceeding the glass transition temperature of the resin contained in the piezoelectric member. The piezoelectric sensitivity still remains lower than its initial value when returned to room temperature after being employed in a high temperature environment exceeding the glass transition temperature.

This drop in piezoelectric sensitivity may be considered in the following manner. The resin (for example polylactic acid) covers fibers in a helical shape. Resin contained in the piezoelectric material is thought to tighten beyond its elastic deformation range when tension is applied in a high temperature environment exceeding the glass transition temperature of the resin. The piezoelectric sensitivity is therefore expected to be lowered by use in a high temperature environment exceeding the glass transition temperature of the resin contained in the piezoelectric material.

However, due the piezoelectric substrate 12C of the present embodiment having a non-circular profile in cross-section perpendicular to its axial center, tightening of the resin is suppressed even were tension to be applied in a high temperature environment exceeding the glass transition temperature of the resin. This is thought to suppress a drop in piezoelectric sensitivity as a result.

Accordingly, the piezoelectric substrate 12C of the present embodiment and the bed device 10 employing the piezoelectric substrate 12C both exhibit excellent piezoelectric sensitivity. In particular, when the piezoelectric substrate 12C is employed in the bed device 10, a drop in piezoelectric sensitivity is suppressed even if the bed device 10 is in a high temperature environment occurring due to high room temperatures in the summer.

The non-circular profile is not particularly limited from the perspective of suppressing tightening of the resin and suppressing a drop in piezoelectric sensitivity, and any non-circular profile may be adopted. Examples of non-circular profiles include elliptical profiles, rectangular profiles, or irregular profiles other than ellipses and rectangles. Such irregular profiles may be triangular, or may be polygonal profiles with five or more sides. The profile may also be cocoon shaped, rhomboidal, or trapezoidal. Of these profiles, an elliptical profile is preferable.

From the perspective of suppressing a drop in piezoelectric sensitivity, the piezoelectric substrate 12C of the present embodiment preferably has a dimensional ratio of its major axis to its minor axis (major axis/minor axis) (also referred to below as "dimensional ratio (major axis/minor axis)" below) of from 1.05 to 10.00 (major axis/minor axis=1.05/1 to 10.00/1) in cross-section perpendicular to its axial center. The dimensional ratio (major axis/minor axis) is more preferably from 1.05 to 5.00, and is even more preferably from 1.05 to 2.00. The dimensional ratio (major axis/minor axis) expresses a ratio in a cross-section perpendicular to the axial center between a minimum length passing through the center of the cross-section profile and the length of an axis perpendicular thereto.

The flattening ratio of the non-circular cross-section may be from 0.4 to 0.9, may be from 0.4 to 0.8, or may be from 0.4 to 0.5. The flattening ratio is determined using the following Equation:

Flattening ratio=(major axis−minor axis)/major axis

Supplement to the Embodiments

In the bed device of each embodiment, the piezoelectric substrate 12 (or the piezoelectric substrate 12A to 12C) may be employed as a biometric information acquisition device. Specifically, the piezoelectric substrate 12 of the present embodiment may be configured as a device to acquire biometric information and be capable of detecting heartrate, pulse, coughing, sneezing, or snoring. For example, the heartrate or pulse can be detected by extracting fluctuating component corresponding to heartrate from the voltage signal output from the piezoelectric substrate 12. As another example, coughing or snoring can be detected by removing low frequency components corresponding to turning over in bed from the voltage signal output from the piezoelectric substrate 12, performing frequency analysis on the voltage signal, and pre-setting a threshold value.

The embodiments may be employed in appropriate combinations thereof, and various aspects may be implemented in a range not departing from the spirit of the present disclosure.

For example, the 20 detection regions 27 of the fourth embodiment may be combined with the piezoelectric substrates 12 of the third embodiment such that the piezoelectric substrates 12 are arranged in wavy shapes in each of the 20 detection regions 27. Alternatively, for example, the piezoelectric substrates 12 in the fifth embodiment may be arranged in the bed lengthwise direction and in the bed width direction alternately in every other detection region 27, instead of arranging the piezoelectric substrates 12 in one of these directions in all of the detection regions 27.

Alternatively, for example, the piezoelectric substrate 12C of the sixth embodiment may be applied to the bed device of any of the second to the fifth embodiments.

The human body detection device 30 of the embodiments may be applied to the following devices instead of the bed device 10. Examples of such devices include a body pressure distribution measurement apparatus or a foot pressure distribution measurement system.

EXAMPLES

More specific explanation follows regarding examples of the present disclosure. There is no limitation to the following examples within a range not departing from the spirit of the present disclosure.

(1) Examples Relating to a Bed Device
Bed Device Manufacture

As illustrated in FIG. 1, the bed device 10 of Example 1 includes the single sized bed 20 configured including the frame 22, the bed boards 24, and the mattress 26. In the bed 20 of Example 1, the sensor unit 32 is arranged between the bed boards 24 and the mattress 26.

The mattress 26 of Example 1 is made of polyurethane, and has a width W of 970 mm, a length L of 2000 mm, and a thickness da of 40 mm. The hardness of the mattress 26 is 150 N according to 6.4 "Method A (method to determine force after 30 seconds at constant 40% compression)" of JIS K 6400-2 (Flexible cellular polymeric materials—Physical properties—Part 2: Determination of hardness and stress-strain characteristics in compression).

Regarding the piezoelectric substrate 12, a piezoelectric film (PLA film) manufactured as described above is formed into microslit ribbon with a thickness of 50 µm and a width of 0.6 mm. Next, the microslit ribbon is wrapped onto a tinsel wire (catalog number: u24) manufactured by Meisei Industry Co., Ltd in an S-winding (counterclockwise) direction at an oblique direction at 45° to the lengthwise direction. As the outer conductor further to the outside thereof, a rolled copper foil with a width of 0.3 mm and a thickness of 30 µm is wrapped densely in a Z winding direction around such that the microslit ribbon is not exposed to the outside so as to produce the piezoelectric substrate 12. The piezoelectric substrate 12 is further covered with the insulating member 38 from above and below in a pressure measurement range of a pressure measurement range spanning 200 mm from one end portion. The insulating member 38 is configured by a polyimide adhesive tape configured by a polyimide film with a thickness of 25 µm, and an adhesive layer with a thickness of 35 µm so as to have a total thickness of 60 µm.

A sheet formed by extruding and expanding polypropylene to approximately three times its volume is applied as the support plate 36. A styrene-butadiene rubber (SBR) sponge sheet with a width of 100 mm and a thickness of 5 mm is applied as the shock absorbing material 37.

On the upper surface of the shock absorbing material 37 thus affixed to the upper surface of the support plate 36, the piezoelectric substrates 12 that are further covered by the insulating member 38 are adhered to each of the regions 34 so as to form the sensor unit 32. The sensor unit 32 of Example 1 is installed on the bed boards 24 so as to straddle between the bed boards 24. Namely, the sensor unit 32 is installed at a bed lengthwise direction central portion.

Figure 13:
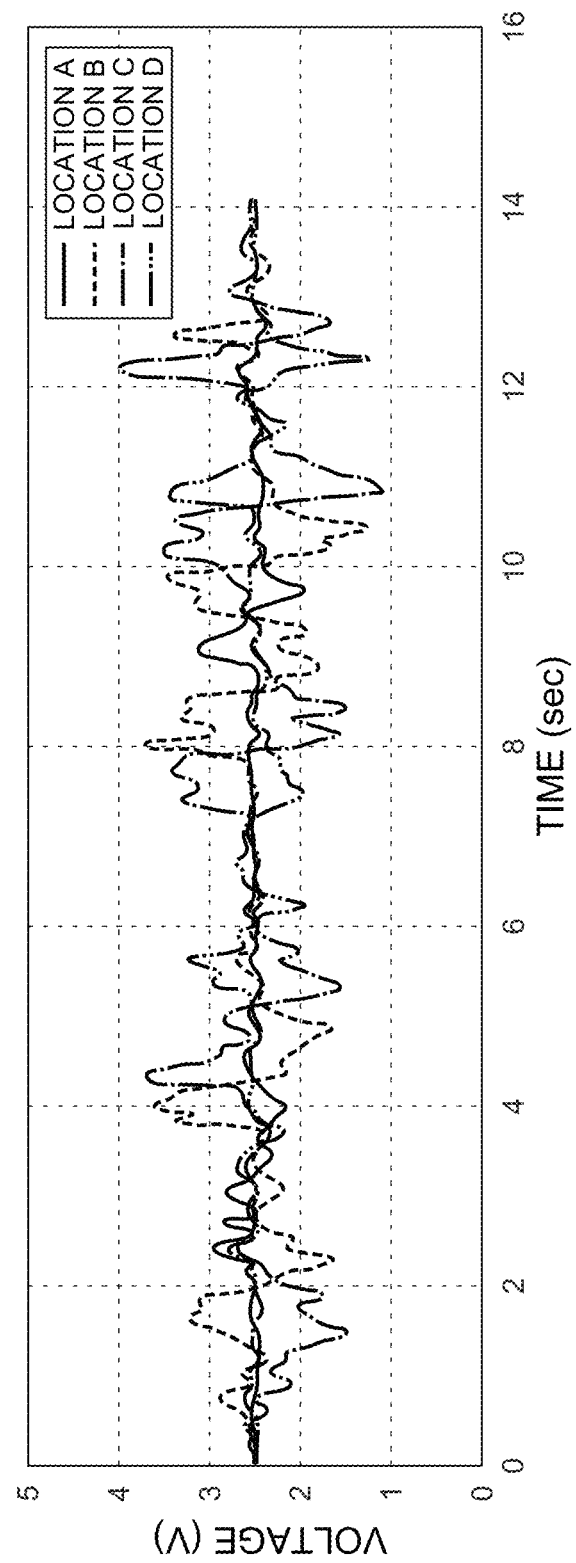
FIG. 13 is a graph illustrating measurement results of voltages output from respective piezoelectric substrates in a bed device of Example 1.

The other end of each of the piezoelectric substrates 12 is configured as a connection electrode, and the inner conductor 16A and the first piezoelectric material 18A are each electrically connected to the AD converter 42 at these connection electrodes.
Confirmation of Detection State A subject, serving as the person in bed, lies on the mattress 26 of the bed device 10, and the subject turns over in sequence between a location A, a location D, the location A, the location D, and a location B starting from a bed width direction central portion (boundary between locations B and C). When this is performed, the voltage output V of the piezoelectric substrates 12 in each of the detection regions 27 is as illustrated in FIG. 13. As illustrated in FIG. 13, the pressure applied to each of the piezoelectric substrates 12 by the mattress 26 itself is expressed as a reference voltage of 2.6 V, and the voltage from the detection regions 27 at the sleeping position of the subject is higher than 2.6 V. The detection regions 27 corresponding to the piezoelectric substrate 12 with the highest voltage value corresponds to the position where the subject is lying.

When the subject turns over in bed, immediately after the subject has moved away the voltage output from the corresponding piezoelectric substrates 12 in the detection region 27 drops below the reference voltage of 2.6 V. This is since the pressure is less from the mattress 26 itself when the mattress 26 that was compression deformed by the body recovers its original shape.

A threshold value Vt is set at 2.9 V, and the moments when this threshold value is exceeded in FIG. 13 are illustrated in FIG. 14. The AD converter 42 of Example 1 is set to output 1 V when the voltage output of the respective piezoelectric substrate 12 exceeds 2.9 V.

In FIG. 13, the sequence of the detection regions 27 corresponding to the piezoelectric substrates 12 that output 1 V is location B, location A, location B, location C, location D, location C, location B, location A, location B, location C, location D, location C, location B, and this matches the sequence of the detection regions 27 when the subject turns over in bed.

Thus Example 1 enables the position on the bed surface of the subject lying on the mattress 26 to be detected, and also enables turning over in bed to be detected.
(2) Examples Relating to Different Cross-Section Profiles of Piezoelectric Substrate The effect of temperature for different cross-section profiles of piezoelectric substrate employed in the bed device was evaluated.
Manufacture of Piezoelectric Material As the helical chiral polymer, 100 parts by mass of polylactic acid (product name: INGEO™ BIOPOLYMER, product code: 4032D) manufactured by NatureWorks LLC were dry blended with a 1 part by mass of stabilizer (a mixture of STABAXOL P400 manufactured by Rhein Chemie Rheinau Gmbh (10 parts by mass), STABAXOL I manufactured by Rhein Chemie Rheinau Gmbh (70 parts by mass), and CARBODILITE LA-1 manufactured by Nisshinbo Chemical Inc. (20 parts by mass)) so as to manufacture the raw material.

The manufactured raw material was placed in an extrusion molder hopper and extruded through a T-die while being heated to 210° C., placed in contact with a cast roller at 50° C. for 0.3 minutes, and formed into a preliminary crystallized sheet with a thickness of 150 µm (a preliminary crystallization process). The degree of crystallinity of the preliminary crystallized sheet was measured to be 6%.

The obtained preliminary crystallized sheet was roll-to-roll processed while being heated to 70° C., and monoaxially stretched at an initial stretching speed of 10 m/min until stretched 3.5 times in an MD direction (a stretching process). The thickness of the obtained film was 49.2 µm.

The monoaxially stretched film was then roll-to-roll processed, and annealed by being made to contact a roller heated to 145° C. for 15 seconds, then rapidly cooled to produce the piezoelectric film (an annealing process).

Next, a slitting machine was employed to slit the piezoelectric film with a slitting direction substantially parallel to the stretching direction of the piezoelectric film. A ribbon shaped piezoelectric material (slit ribbon) with width of 0.39 mm and a thickness of 50 µm was obtained thereby. Note that the obtained piezoelectric material has a rectangular cross-section profile.

The glass transition temperature of the piezoelectric material obtained was 68.8° C.

Measurement of Physical Properties of Piezoelectric Material

The physical properties of the ribbon shaped piezoelectric material obtained as described above were measured as follows. The results thereof are listed in Table 1.

Measurement was performed using a wide-angle X-ray diffractometer (RINT 2550 manufactured by Rigaku Corporation, attachment device: rotational sample table, X-ray source CuKα, output: 40 kV, 370 mA, detector: scintillation counter). The sample (piezoelectric material) was fixed in a holder, and peaks in the azimuthal distribution of strength at the crystal faces ((110) face/(200) face) was measured.

The degree of crystallinity and the half width (a) of the peak in the obtained azimuthal distribution curve (X-ray interferogram) were used to compute the degree of orientation F (degree of orientation in the C axis) of the polylactic acid using the following Equation. The results were a degree of crystallinity of 45% and a degree of orientation F of 0.97.

$$\text{Degree of orientation } (F) = (180° - \alpha)/180°$$

(wherein α represents the half width of the peak derived from orientation).

| Piezoelectric Material | | | |
|---|---|---|---|
| Material | Form | Degree of Crystallinity | Degree of Orientation F |
| polylactic acid | slit ribbon | 45% | 0.97 |

Relative Permittivity of Piezoelectric Material

Measurement was performed in accordance with JIS C2151 (2006) using a permittivity measurement device (Precision LCR meter HP4284A, manufactured by Agilent Technologies, Inc.) with a measurement frequency of 1 kHz, in a test environment of 22° C. and 60% RH. The result was a relative permittivity εS of 2.75 for the piezoelectric material (slit ribbon).

Example 2

Manufacture of Piezoelectric Substrate

The piezoelectric substrate provided with a copper foil ribbon as the outer conductor (ground conductor) was manufactured by the following method.

First, a tinsel wire U24-01-00 (external diameter 0.3 mm, length 250 mm) manufactured by Meisei Industry Co., Ltd was prepared as the inner conductor (signal line conductor).

The tinsel wire employed was configured by a meta-aramid fiber (two twisted threads with a yarn count of 40) as the central thread with rolled two copper foil (width 0.3 mm×thickness 0.02 mm) helically wound in a left-handed manner around the central thread two layers thick at 22 windings per 10 mm, such that the central thread is not exposed.

Press-fit terminals were crimped as electrical connection portions and mechanical connection portions onto both ends of the prepared tinsel wire.

Next, the ribbon shaped piezoelectric material (slit ribbon) obtained as described above with a width of 0.6 mm and a thickness of 49.2 μm was wound in a left-handed manner in a direction at 45° with respect to the lengthwise direction of the tinsel wire (helix angle of) 45° around the tinsel wire to enclose the tinsel wire with no gaps such that the tinsel wire was not exposed and not visible.

Note that "winding in a left-handed manner" refers to winding the ribbon shaped piezoelectric material in a left-handed manner from the near side to the far side of the signal line conductor (tinsel wire) when the signal line conductor is viewed from one axial direction end (the right end side in FIG. 6A).

Next, Aronalpha (cyanoacrylate adhesive) 911P2 manufactured by Toagosei Co., Ltd. was dripped onto and impregnated as an adhesive into a wound portion of the ribbon shaped piezoelectric material to form a functional layer in order to mechanically integrate the tinsel wire and the ribbon shaped piezoelectric material together.

Next, an adhesive-coated copper foil ribbon slit to a 0.6 mm width was prepared as the outer conductor. Using a similar method to that for the ribbon shaped piezoelectric material, the copper foil ribbon was wound around the ribbon shaped piezoelectric material without any gaps therebetween such that the ribbon shaped piezoelectric material was enclosed and not exposed.

Next, after enclosing the outer electrode, a heat press (manufactured by Imoto Machinery Co., LTD, model number: IMC-1945-A) was used to hot press an axial direction length thereof of 50 mm at a temperature of 80° C. and a pressure of 14 MPa for 20 minutes. The profile in a cross-section perpendicular to its axial center was a flattened elliptical profile such as that illustrated in FIG. 15B. This hot pressing resulted in a piezoelectric material with a major axis of 0.497 mm, a minor axis of 0.312 mm (major axis/minor axis dimensional ratio=1/1.59), and a flattening ratio of 0.372 being obtained. The flattening ratio was determined using the following Equation.

$$\text{Flattening ratio} = (\text{major axis} - \text{minor axis})/\text{major axis}$$

The piezoelectric material of Example 2 was obtained as described above.

The tinsel wire corresponds to the inner conductor 16A in FIG. 15A. The ribbon shaped piezoelectric material corresponds to the first piezoelectric material 18A illustrated in FIG. 15A. Although not illustrated in FIG. 15A, adhesive is arranged between the inner conductor 16A and the first piezoelectric material 18A. Likewise, the ground conductor is also not illustrated in FIG. 15A.

Example 3

A piezoelectric material of Example 3 was obtained in a similar manner to Example 2, with the exception that adhesive to integrate the tinsel wire and the ribbon shaped piezoelectric material together was not applied, and hot pressing was not performed.

Temperature Characteristic Evaluation

The electrical charge generated (amount of charge generated) in the piezoelectric materials of Example 2 and Example 3 when applied with tension was measured, and the amount of charge generated per unit tension (hereafter referred to as the "sensitivity") was computed from the amount of charge generated. When doing so, the sensitivity was computed at multiple locations at temperatures from 25° C. to 80° C., and temperature characteristics obtained by repetition for three cycles thereof. The computed results for Example 2 are illustrated in FIG. 16A, and the computed results for Example 3 are illustrated in FIG. 16B.

As illustrated in FIG. 16A, in the first cycle the piezoelectric substrate of Example 2 exhibited a small change in sensitivity over a range from 25° C. to 50° C., an increased sensitivity compared to the initial values over a range from 50° C. to 70° C. (including a peak value at 60° C.), and a drop in sensitivity over a range from 70° C. to 80° C. The polylactic acid configuring the piezoelectric substrate of the present Example had a glass transition temperature of about 60° C., and so there was a drop in sensitivity as the temperature rose to a temperature region of 60° C. and above. Moreover, in the second cycle, the piezoelectric substrate of Example 2 exhibited a small change in sensitivity over a range from 25° C. to 60° C., and a drop in sensitivity over a range from 60° C. to 80° C. Temperature characteristics were obtained for the piezoelectric substrate of Example 2 in the third cycle that were substantially the same as those of the second cycle.

It is apparent from the above that the piezoelectric material of Example 2 exhibited stable temperature characteristics due to repeated cycling between 25° C. and 80° C. This is thought to be because, from the second cycle onward, the sensitivity at 25° C. returned to the initial value after being measured at 80° C. It is accordingly apparent therefrom that the piezoelectric material of Example 2 has excellent sensitivity.

The reason why Example 2 exhibited different temperature characteristics only in the first cycle compared to those of the second cycle onward is thought to be possibly due to gap that arise in pressing, such as when molding, stretching under tension in the first cycle, but not stretching from the second cycle onward, so that the temperature characteristics stabilized.

As illustrated in FIG. 16B, the piezoelectric substrate of Example 3 exhibited a small change in sensitivity in the first cycle over a range from 25° C. to 60° C., and a drop in sensitivity over a range from 60° C. to 80° C. An overall drop in the sensitivity over the range from 25° C. to 60° C. also occurred due to repeating for the second cycle and the third cycle.

The reason why the temperature characteristics of the piezoelectric material of Example 3 are not stable is thought to be that after being measured at 80° C., the width of the ribbon shaped piezoelectric material widens and the wire diameter thereof decreases. Namely, the extent of tightening of the ribbon shaped piezoelectric material is thought to change depending on the ambient temperature.

Note that in Example 2 and Example 3, the width of the ribbon shaped piezoelectric material was observed using a microscope on the piezoelectric material before and after the temperature characteristic evaluation. As a result a reduction of approximately 0.026% in the width of the ribbon shaped piezoelectric material was observed in the piezoelectric substrates of Example 2. This tells us that a change in the tightening of the ribbon shaped piezoelectric material is not seen in the piezoelectric substrate of Example 2 even after being measured at 80° C.

However, in the ribbon shaped piezoelectric material of Example 3, the width of the ribbon shaped piezoelectric material was confirmed to have increased by approximately 15%, while a further reduction in the wire diameter was also observed. It is apparent therefrom that, in the piezoelectric substrate of Example 3, the ribbon shaped piezoelectric material clearly has undergone a change in tightening after being measured at 80° C.

The disclosure of Japanese Patent Application No. 2018-175421, filed on Sep. 19, 2018, is incorporated in its entirety by reference herein.

All cited documents, patent applications, and technical standards mentioned in the present specification are incorporated by reference in the present specification to the same extent as if each individual cited document, patent application, or technical standard was specifically and individually indicated to be incorporated by reference.

EXPLANATION OF THE REFERENCE NUMERALS 10, 10A, 10B, 10C, 10D bed device (human body detection system)
12 piezoelectric substrate (biometric information acquisition device)
16A inner conductor (conductor)
18A first piezoelectric material (piezoelectric material)
24 bed board (plate material)
26 mattress (pressing section)
30 human body detection device
33 reference plane
34 region
37 shock absorbing material (base portion)
38 insulating member (covering member)
55 detection section
56 determination section

The invention claimed is:

1. A human body detection device comprising:
line-shaped piezoelectric substrates respectively provided in each of a plurality of regions in a plate material intersecting a direction of pressure received from a human body, and provided such that an axial direction of each of the piezoelectric substrates runs along the plate material so as to detect pressure applied in a radial direction of the piezoelectric substrate;
a pressing section running along the plate material so as to contact the piezoelectric substrates and be pressed by contact with the human body;
a plurality of shock absorbing materials that are in contact with the piezoelectric substrates for each piezoelectric substrate and are disposed on an opposite side from the pressing section with the piezoelectric substrates therebetween, wherein each of the plurality of shock absorbing materials is smaller than a respective region of the plurality of regions, and wherein the shock absorbing materials are placed separately from each other;
memory; and
a processor coupled to the memory, the processor being configured to be capable of detecting an output signal from each of the piezoelectric substrates.

2. The human body detection device of claim 1, wherein:
each of the piezoelectric substrates includes
an elongate conductor, and
an elongate piezoelectric material helically wound in one direction around the conductor; and
pressure input to the piezoelectric material is detected from a difference in potential between the conductor and the piezoelectric material.

3. The human body detection device of claim 2, wherein an organic piezoelectric material is employed as the piezoelectric material.

4. The human body detection device of claim 3, wherein the piezoelectric material is an optically active helical chiral polymer (A).

5. The human body detection device of claim 4, wherein the helical chiral polymer (A) is polylactic acid.

6. The human body detection device of claim 2, wherein each of the piezoelectric substrates includes a covering member at a periphery of the piezoelectric material.

7. The human body detection device of claim 1, further comprising:

a base portion adjacent to the piezoelectric substrates and on a side facing toward the pressing section.

8. The human body detection device of claim 7, wherein a thickness of the pressing section is in a range of from 0.005 mm to 200 mm, and a hardness of the pressing section is in a range of from 50 N to 200 N as measured in accordance with Method A defined in JIS K 6400-2.

9. The human body detection device of claim 7, wherein the pressing section, the piezoelectric substrates, and the base portion are arranged along a direction in which the pressing section is pressed.

10. The human body detection device of claim 7, wherein a foamed plastic is employed as the base portion.

11. The human body detection device of claim 1, wherein each of the piezoelectric substrates is a biometric information acquisition device.

12. The human body detection device of claim 1, wherein each of the piezoelectric substrates has a non-circular cross-section profile in a cross-section taken perpendicular to the axial direction of the piezoelectric substrate.

13. The human body detection device of claim 12, wherein, in a cross-section taken perpendicular to the axial direction of the piezoelectric substrate, each piezoelectric substrate has a dimensional ratio of a major axis with respect to a minor axis of from 1.05 to 10.00.

14. A bed device comprising the human body detection device of claim 1.

15. A human body detection system comprising:
the human body detection device of claim 1;
the regions provided along a predetermined direction in the plate material; and
the piezoelectric substrates arranged in each of the regions,
wherein the processor is configured to determine movement of the human body above the plate material by comparing output signals from piezoelectric substrates that are adjacent to each other in the predetermined direction.

* * * * *